(12) United States Patent
Kattman et al.

(10) Patent No.: US 9,181,529 B2
(45) Date of Patent: *Nov. 10, 2015

(54) TITRATION OF DIFFERENTIATION MEDIUM COMPONENTS

(75) Inventors: Steven Kattman, Madison, WI (US); Wen Bo Wang, Waunakee, WI (US); Peter Fuhrken, Madison, WI (US); Nathan Meyer, Mazomanie, WI (US); Matthew George, Fitchburg, WI (US); Casey Stankewicz, Madison, WI (US)

(73) Assignee: Cellular Dynamics International, Inc., Madison, WI (US)

(*) Notice: Subject to any disclaimer, the term of this patent is extended or adjusted under 35 U.S.C. 154(b) by 950 days.

This patent is subject to a terminal disclaimer.

(21) Appl. No.: 13/276,832

(22) Filed: Oct. 19, 2011

(65) Prior Publication Data

US 2012/0129211 A1 May 24, 2012

Related U.S. Application Data

(60) Provisional application No. 61/394,589, filed on Oct. 19, 2010.

(51) Int. Cl.
  *C12N 5/00* (2006.01)
  *C12N 5/02* (2006.01)
  *C12N 5/074* (2010.01)

(52) U.S. Cl.
  CPC ............ *C12N 5/0696* (2013.01); *C12N 5/0607* (2013.01); *C12N 2503/00* (2013.01); *C12N 2506/00* (2013.01)

(58) Field of Classification Search
  CPC . C12N 5/0607; C12N 5/0696; C12N 2506/00
  See application file for complete search history.

(56) References Cited

U.S. PATENT DOCUMENTS

| | | | |
|---|---|---|---|
| 6,602,711 B1 | 8/2003 | Thomson et al. | 435/378 |
| 7,727,762 B2 | 6/2010 | Fukuda et al. | 435/377 |
| 7,763,464 B2 | 7/2010 | Xu | 435/377 |
| 7,781,214 B2 | 8/2010 | Smith et al. | 435/377 |
| 2003/0211603 A1 | 11/2003 | Earp et al. | 435/366 |
| 2007/0238170 A1 | 10/2007 | Thomson et al. | 435/366 |
| 2008/0038820 A1 | 2/2008 | Rudy-Reil | 435/377 |
| 2008/0113433 A1 | 5/2008 | Robins et al. | 435/377 |
| 2008/0171385 A1 | 7/2008 | Bergendahl et al. | 435/366 |
| 2008/0226558 A1 | 9/2008 | Keller et al. | 424/9.1 |
| 2008/0254003 A1 | 10/2008 | Passier et al. | 424/93.7 |
| 2009/0047739 A1 | 2/2009 | Gold et al. | 435/377 |
| 2010/0317104 A1* | 12/2010 | Elefanty et al. | 435/366 |
| 2011/0097799 A1 | 4/2011 | Stankewicz et al. | 435/377 |
| 2012/0276063 A1 | 11/2012 | Meyer et al. | |

FOREIGN PATENT DOCUMENTS

| | | |
|---|---|---|
| EP | 1783205 | 5/2007 |
| EP | 2 014 766 | 1/2009 |
| KR | 10-2009-0090586 | 8/2009 |
| WO | WO 01/51616 | 7/2001 |
| WO | WO 03/004626 | 1/2003 |
| WO | WO 2007/002136 | 1/2007 |
| WO | WO 2008/035110 | 3/2008 |
| WO | WO 2008/106771 | 9/2008 |
| WO | WO 2009/120762 | 10/2009 |
| WO | WO 2010/007031 | 1/2010 |
| WO | WO 2010/063848 | 6/2010 |

OTHER PUBLICATIONS

Schuldiner et al. PNAS 97(21):11307-11312, 2000.*
Kehoe et al. Tissue Engineering: Part A 16(2):405-421, online Sep. 9, 2009.*
Chambers et al., "Highly efficient neural conversion of human ES and iPS cells by dual inhibition of SMAD signaling," *Nature Biotechnology*, 27:275-281, 2009.
Chen et al., "Chemically defined conditions for human iPSC derivation and culture," *Nature Methods* 8:424-429, 2011.
Chen et al., "Integration of external signaling pathways with the core transcriptional network in embryonic stem cells," *Cell*, 133:1106-1117, 2008.
Cohen et al., "The role of FGF-signaling in early neural specification of human embryonic stem cells," *Developmental Biology*, 340:450-458, 2010.
Greber et al., "FGF signaling inhibits neural induction in human embryonic stem cells," *The EMBO Journal*, 30:4874-4884, 2011.
Greber et al., "Fibroblast growth factor 2 modulates transforming growth factor beta signaling in mouse embryonic fibroblasts and human ESCs (hESCs) to support hESC self-renewal," *Stem Cells*, 25:455-464, 2007.
Kattman et al., "Stage-specific optimization of activin/nodal and BMP signaling promotes cardiac differentiation of mouse and human pluripotent stem cell lines," *Cell Stem Cell*, 8:228-240, 2011.
Kim et al., "Dopamine neurons derived from embryonic stem cells function in an animal model of Parkinson's disease," *Nature*, 418:50-56, 2002.
Krencik and Zhang, "Specification of transplantable astroglial subtypes from human pluripotent stem cells," *Nature Biotechnology* 29:528-534, 2011.
Krencik et al., "Directed differentiation of functional astroglial subtypes from human pluripotent stem cells," *Nature Protocols* 6(11):1710-1717, 2011.
Li et al., "Rapid induction and long-term self-renewal of primitive neural precursors from human embryonic stem cells by small molecule inhibitors," *PNAS*, 108(20):8299-8304, 2011.
Office Action issued in U.S. Appl. No. 13/435,698, mailed Dec. 21, 2012.

(Continued)

*Primary Examiner* — Marcia S Noble
(74) *Attorney, Agent, or Firm* — Parker Highlander PLLC

(57) ABSTRACT

Methods and composition for differentiation of pluripotent stem cells are provided. For example, in certain aspects methods including screening of optimal differentiation conditions for a selected stem cell clone in a selected batch of culture medium and use of the determined optimal condition for differentiation into a specific cell lineage.

37 Claims, 1 Drawing Sheet

(56) References Cited

OTHER PUBLICATIONS

Ogawa et al., "Activin-Nodal signaling is involved in propagation of mouse embryonic stem cells," *J. Cell Sci.*, 120:55-65, 2007.
PCT International Search Report and Written Opinion issued in International Application No. PCT/US2012/031457, mailed Sep. 25, 2012.
Smukler et al., "Embryonic stem cells assume a primitive neural stem cell fate in the absence of extrinsic influences," *The Journal of Cell Biology*, 172(1):79-90, 2006.
Stavridis et al., "A discrete period of FGF-induced Erk1/2 signalling is required for vertebrate neural specification," *Development*, 134:2889-2894, 2007.
Sterneckert et al., "Neural induction intermediates exhibit distinct roles of Fgf signaling," *Stem Cells*, 28:1772-1781, 2010.
Suzuki et al., "Nanog binds to Smad1 and blocks bone morphogenetic protein-induced differentiation of embryonic stem cells," *Proc. Natl. Acad. Sci. USA*, 103:10294-10299., 2006.
Tropepe et al., "Direct neural fate specification from embryonic stem cells: a primitive mammalian neural stem cell stage acquired through a default mechanism," *Neuron*, 20:65-78, 2001.
Watabe and Miyazono, "Roles of TGF-beta family signaling in stem cell renewal and differentiation," *Cell Res.*, 19:103-115, 2009.
Xu et al., "NANOG is a direct target of TGFbeta/activin-mediated SMAD signaling in human ESCs," *Cell Stem Cell*, 3:196-206., 2008.
Bauwens et al., "Control of human embryonic stem cell colony and aggregate size heterogeneity influences differentiation trajectories," *Stem Cells*, 26(9):2300-10, 2008.
Boheler et al., "Differentiation of pluripotent embryonic stem cells into cardiomyocytes," *Circulation Research*, 91:189, 2002.
Carpenedo et al., "Rotary suspension cultue enhances the efficiency, yield, and homogeneity of embryoid body differentiation," *Stem Cells*, 25(9):2224-34, 2007.
Claassen et al., "ROCK inhibition enhaces the recovery and growth of cryopreserved human embryonic stem cells and human induced pluripotent stem cells," *Mol. Reprod. Dev.*, Epub ahead of print, Feb. 20, 2009, pp. 722-732.
Gai et al., "Generation and characterization of functional cardiomyocytes using induced pluripotent stem cells derived from human fibroblasts," *Cell Biology International*, 33:1184-1193, 2009.
Hao et al., "Dorsomorphin, a selective small molecule inhibitor of BMP signaling, promotes cardiomyogenesis in embryonic stem cells," *PLoS One*, 3(8):e2904, 2008. 8 pages.
Harb et al., "The Rho-Rock-Myosin signaling axis determines cell-cell integrity of sel-renewing pluripotent stem cells," *PLoS ONE*, 3(8):e3001, 2008.
Kim et al., "Use of long-term cultured embryoid bodies may enhance cardiomyocyte differentiation by BMP2," *Yonsei Med. J.*, 49(5):819-827, 2008.
Krawetz et al., "Human embryonic stem cells: caught between a ROCK inhibitor and a hard place," *Bioessays*, 31(3),336-43, 2009.
Laflamme et al., "Cardiomyocytes derived from human embryonic stem cells in pro-survival factors enhance function of infracted rat hearts," *Nature Biotechnology*, 25(9):1015-24, 2007.
Lev et al., "Differentiation pathways in human embryonic stem cell-derived cardiomyocytes," *Ann. N.Y. Acad. Sci.*, 1047:50-65, 2005.
Mauritz et al., "Generation of functional murine cardiac myocytes from induced pluripotent stem cells," *Circulation*, 118:507-517, 2008.
Narazaki et al., "Directed and systematic differentiation of cardiovascular cells from mouse induced pluripotent stem cells," *Circulation*, 118(5):498-506, 2008.
Niebruegge et al., "Cardiomyocyte production in mass suspension culture: embryonic stem cells as a source for great amounts of functional cardiomyocytes," *Tissue Engineering: Part A*, 14(10):1591-1601, 2008.
Niebruegge et al., "Generation of human embryonic stem cell-derived mesoderm and cardiac cells using size-specified aggregates in an oxygen-controlled bioreactor," *Biotechnology and Bioengineering*, 102(2):493-507, 2009.
Pandur, "What does it take to make a heart," *Biology of the Cell*, 97:197-210, 2005.
Pucéat, "Protocols for cardiac differentiation of embryonic stem cells," *Methods*, 45:168-171, 2008.
Sargent et al., "Cardiomyogenic differentiation of embryoid bodies is promoted by rotary orbital suspension culture," *Tissue Engineering: Part A*, 15(2):331-342, 2009.
Takei et al., "Bone morphogenetic protein-4 promotes induction of cardiomyocytes from human embryonic stem cells in serum-based embryoid body development," *Am. J. Physiol. Heart Circ. Physiol.*, 296:H1793-H1803, 2009.
Ungrin et al., "Reproducible, ultra high-throughput formation of multicellular organization from single cell suspension-derived embryonic cell aggregates," *PLoS ONE.*, 3(2):e1565, Feb. 2008. 12 pages.
Watanabe et al., "A ROCK imhibitor permits survival of dissociated human embryonic stem cells," *Nat. Biotechnol.*, 25(6):681-6, 2007.
Xu et al., "Characterization and enrichment of cardiomyocytes derived from human embryonic stem cells," *Circulation Research*, 91;501-508, 2002.
Zandstra et al., "Scalable production of embryonic stem cell-derived cardiomyocytes," *Tissue Engineering*, 9(4):767-778, 2003.
Zhang et al., "[Differentiating into endothelioid cells from murine embryonic stem cell]," *Zhongguo Xiu Fu Chong Jian Wai Ke Za Zhi*, 23(1):82-86, 2009. (English abstract).
Zhang et al., "Functional cariomyocytes derived from human induced pluirpotent stem cells," *Circulation Research*, 104:e30-e41, 2009.

\* cited by examiner

TITRATION OF DIFFERENTIATION MEDIUM COMPONENTS

This application claims the benefit of U.S. Provisional Patent Application No. 61/394,589, filed Oct. 19, 2010, the entire contents of which are incorporated herein by reference. The subject matter of this application relates to that of U.S. patent application Ser. No. 12/907,714 (titled "Cardiomyocyte Production" by Casey Stankewicz, Matt Riley, Nathaniel Beardsley, Wen Bo Wang, Peter Fuhrken and Steven Kattman) filed on Oct. 19, 2010, the entire contents of which are incorporated herein by reference in its entirety without disclaimer.

BACKGROUND OF THE INVENTION

1. Field of the Invention

The present invention relates generally to the field of stem cell development. More particularly, it concerns the induction of selected lineage differentiation from pluripotent stem cells.

2. Description of Related Art

Pluripotent stem cells, such as induced pluripotent stem cells (iPS) cells, are a potential source of cells for production of specific lineage of differentiated cells. Differentiation of pluripotent stem cells can be achieved either spontaneously or upon induction.

However, a number of obstacles have stood in the way of developing a paradigm for obtaining substantially enriched populations of specific lineage cells from pluripotent stem cells. Some ensue from the relative fragility of pluripotent cells of primate origin, the difficulty in culturing them, their exquisite sensitivity and dependence on various factors present in the culture environment, and low efficiency and wide variation of differentiation methods. Thus, there is a need to improve differentiation of pluripotent stem cells to specific lineage of cells, especially for large-scale or high efficiency production.

SUMMARY OF THE INVENTION

The present embodiments overcome a major deficiency in the art by providing methods for differentiating pluripotent stem cells into specific lineage of cells, especially for high efficiency and large scale production to meet the needs in clinical applications.

Procedures for differentiating pluripotent stem cells preferably employ culture conditions that attempt to mimic the in vivo environment driving the development of a particular lineage, such as by the addition of specific growth factors. When differentiated in vitro, a number of sources contribute to the growth factor environment, including: 1) endogenous expression from the cells themselves, 2) the sera and/or media that the pluripotent stem cells are cultured and/or subsequently differentiated, and 3) the addition of exogenous growth factors. In regard to the endogenous expression of growth factors, this can arise from clone-to-clone variability and from differences in the primary culture of the cells. Furthermore, the inventors have determined that there exists (sometimes dramatic) batch-to-batch variability in the growth factor content of the culture medium used in culturing and differentiation of pluripotent stem cells, both introducing unpredictability to cell lineage differentiation.

In order to address the foregoing variability in pluripotent stem cell differentiation procedures, the present inventors have developed a technique which accounts for all the sources contributing to the growth factor environment in a given differentiation culture, which are independently "balanced" for each batch or lot of medium and for each individual stem cell clone that is employed, in order to achieve an optimal differentiation. This may be achieved by the addition of differentiation factors to modulate developmental signaling pathways. Examples include: 1) the addition of antagonists to reduce the total signal in certain pathways, 2) the addition of agonists to increase the total signal of certain pathways or 3) combinations of agonists and or antagonists to optimize the signal.

Thus, there may be provided a method for differentiating stem cells from a selected pluripotent stem cell clone into a selected cell lineage. The method may comprise differentiating the stem cells into the selected cell lineage in a differentiation medium prepared from a selected batch of culture medium. In certain aspects, the differentiation medium has been prepared from the selected batch of culture medium by adjusting the amounts or timing of addition of one or more differentiation factors in a culture medium from the selected batch at amounts or timing determined to be appropriate for differentiation of the selected pluripotent stem cell clone into the selected cell lineage and selected batch of culture media employed. For example, the selected pluripotent stem cell clone is an induced pluripotent stem (iPS) cell clone.

Without wishing to be bound by theory, it may be contemplated that TGFβ signaling pathways may be delicately regulated to achieve the optimal differentiation condition. In particular, BMP signaling and Activin signaling may be two exemplary TGFβ signaling pathways that could be optimized. The relative activity ratio between the two signaling pathways may be important for the optimal differentiation condition. Thus, differentiation factors may include positive modulators or inhibitors of BMP signaling and/or Activin signaling. For example, BMP signaling inhibitor comprises dorsomorphin and Activin signaling inhibitor comprises SB431542.

Non-limiting examples of differentiation factors which are adjusted in the culture medium include one or more of modulators of signaling pathways of bone morphogenetic protein, ActivinA/Nodal, vascular endothelial growth factor (VEGF), dickkopf homolog 1 (DKK1), basic fibroblast growth factor (bFGF), insulin growth factor (IGF), and/or epidermal growth factor (EGF). For example, the differentiation factors may comprise BMP2, BMP4, BMP 10, Activin A, bFGF, IGF, EGF, BMP signaling inhibitor, Activin signaling inhibitor, or a combination thereof.

In certain aspects, the differentiation medium may have been prepared from the selected batch of culture medium by adjusting the amounts of addition of one or more differentiation factors, such as for differentiation of cardiomyocytes or hepatocytes. In further aspects, the differentiation medium may have been prepared from the selected batch of culture medium by adjusting the timing of addition of one or more differentiation factors, such as for differentiation of neurons.

There may provided a method involving separately determining the appropriate amount and/or timing of growth factors that should be added for any given medium batch and pluripotent cell clone employed. Once the adjustment is determined for the particular medium batch and cell clone, the adjustment is incorporated into the differentiation procedure, providing a highly reproducible differentiation procedure tailored for each batch and clone.

In certain aspects, the method may comprise determining amounts of addition of one or more differentiation factors appropriate for differentiation into selected lineages, such as cardiomyocytes, neurons or hepatocytes. This determination may comprise testing differentiation of cells from the selected clone in a culture medium from the selected batch added with varied amounts of differentiation factors during a test period. For example, varied amounts of differentiation factors may be added during a test period. The test period may be the same or varied for a test condition with a specific concentration of differentiation factors. For example, the test period may start from about 1, 2, 3, 4, 5, 6, 7 prior to differentiation or day 1, 2, 3, 4, 5 after differentiation, and end on day 6, 7, 8, 9, 10, 11, 12, or 13 after differentiation (any intermediate time period may also be included). The same concentration of differentiation factors may be changed daily or every 2, 4, 8, 16, 24, 48 hours or any intermediate intervals.

Such varied amounts of differentiation factors may include conditions with varied ratios of BMP/Activin signaling activity. This may be achieved by varying amounts of BMP, Activin, BMP signaling inhibitor, and/or Activin signaling inhibitor. For example, this variation may include one or more of the following varying conditions: varied concentrations of BMP4 alone, varied concentration of Activin A alone, varied concentration of BMP signaling inhibitor, varied concentration of Activin signaling inhibitor, and varied concentration of combination of BMP4 and Activin A.

To determine the appropriate cardiomyocyte differentiation condition, the testing may further comprise measuring mesoderm or cardiomyocyte differentiation efficiency for each condition and selecting the condition with the highest differentiation efficiency as being appropriate for the differentiation of the selected pluripotent stem cell clone into cardiomyocytes and selected batch of culture media employed. The measurement of differentiation efficiency may comprise measuring mesoderm marker expression at least or about days 5, 6, 7, 8, 9, 10, 11, 12, 13 after differentiation or any intermediate time range. Non-limiting examples of mesoderm markers include KDR, PDGFR-a, CXCR4, CKIT$^{negative}$, N-Cadherin, and/or MESP1. In other aspects, the measurement of differentiation efficiency may comprise measuring differentiation efficiency comprises measuring cardiomyocyte marker expression at about or at least day 14 after differentiation. After selection of the appropriate condition, the method may comprise differentiating the stem cells into cardiomyocytes in a differentiation medium prepared from a selected batch of culture medium, wherein the differentiation medium has been prepared from the selected batch of culture medium under the selected condition during the test period.

The selected cell lineage may be that of hepatocytes. In certain aspects, the method may further comprise determining amounts of addition of one or more differentiation factors appropriate for differentiation into hepatocytes. The determination may comprise testing differentiation of cells from the selected clone in a culture medium from the selected batch added with varied amounts of differentiation factors during a test period. The test period may start from about 1, 2, 3, 4, 5, 6, 7 prior to differentiation or day 1, 2, 3, 4, 5 after differentiation, and end on day 6, 7, 8, 9, 10, 11, 12, or 13 after differentiation (any intermediate time period may also be included).

Such varied amounts of differentiation factors may include conditions with varied ratios of BMP/Activin signaling activity. This may be achieved by varying amounts of BMP, Activin, BMP signaling inhibitor, and/or Activin signaling inhibitor. For example, this variation may include one or more of the following varying conditions: varied concentrations of BMP4 alone, varied concentration of Activin A alone, varied concentration of BMP signaling inhibitor, varied concentration of Activin signaling inhibitor, and varied concentration of combination of BMP inhibitor and Activin A.

To determine the appropriate hepatocyte differentiation condition, the testing may comprise measuring endoderm or hepatocyte differentiation efficiency for each condition and selecting the condition with the highest differentiation efficiency as being appropriate for the differentiation of the selected pluripotent stem cell clone into hepatocytes and selected batch of culture media employed. The measurement may comprise measuring endoderm marker expression or hepatocyte marker expression. After selection of the appropriate condition, the method may comprise differentiating the stem cells into hepatocytes in a differentiation medium prepared from a selected batch of culture medium, wherein the differentiation medium has been prepared from the selected batch of culture medium under the selected condition during the test period.

The selected cell lineage may be that of neurons. It has been determined that timing of addition of differentiation factors may be important for neuron differentiation. For example, addition of differentiation factors prior to the beginning of differentiation may prepare pluripotent stem cells more prone to neural differentiation. Thus, the timing of addition of differentiation factors to the specific culture medium for culturing of a selected pluripotent stem cell clone may be screened. In a further aspect, the method may comprise determining amounts of addition of one or more differentiation factors appropriate for differentiation into neurons when combined with testing of variable testing periods.

In further aspects, the method may comprise determining timing of addition of one or more differentiation factors appropriate for differentiation into selected lineages, such as neurons. The determination may comprise testing differentiation of cells from the selected clone in a culture medium from the selected batch with differentiation factors added during varied test periods. Such differentiation factors may include BMP signaling inhibitor, and/or Activin signaling inhibitor. The varied test periods used in timing determination may be varied periods that start prior to differentiation, such as two or more of the following conditions: day 5 prior to differentiation to day 0, day 4 prior to differentiation to day 0, day 3 prior to differentiation to day 0, day 2 prior to differentiation to day 0, and day 1 prior to differentiation to day 0. The concentration of differentiation factors may be also varied in varied test periods to determine an appropriate combination of levels and timing of addition of differentiation factor(s).

For determination of the appropriate neural differentiation timing of addition of differentiation factors, the testing may comprise measuring neural differentiation efficiency for each test period and selecting the test period with the highest differentiation efficiency as being appropriate for the differentiation of the selected pluripotent stem cell clone into neurons and the selected batch of culture media employed. After selection of the appropriate neural differentiation timing, the method may comprise differentiating the stem cells into neurons in a differentiation medium, wherein the differentiation medium has been prepared from the selected batch of culture medium by adding differentiation factors during the selected test period.

The methods may be suited for large scale production of selected cell lineage in a suspension culture. Pluripotent stem cells or progeny cells thereof may be incubated in a suspension culture. Pluripotent stem cell aggregates may be formed in a suspension culture. The suspension culture may have a volume of about, at least or at most 2 ml, 5 ml, 10 ml, 20 ml, 30 ml, 40 ml, 50 ml, 100 ml, 200 ml, 500 ml, 1 liters, 3 liters, 5 liters, 10 liters, 20 liters, 25 liters, 30, liters, 40 liters, 50 liters, or any range derivable therein, such as in a bioreactor. Some embodiments involve cells growing in a space whose volume is larger than a standard petri dish or 96-well plate; consequently, some embodiments exclude the use of such containers.

In certain embodiments of the invention, large scale production of selected cell lineages may be implemented. "Large scale," as used herein, refers to the use of a cell culture of a volume of at least 500 ml with a concentration of at least $1.0 \times 10^6$ cells/ml. The volume may be at least or about 500 ml, 600 ml, 700 ml, 800 ml, 1 liter, 2 liters, 3 liters, 5 liters, 10 liters, 20 liters, or up to 25 liters, or any range derivable therein, such as in a bioreactor. Cell concentration in suspension culture may be at least or about $10^6$, $10^7$, $10^8$, $10^9$, $10^{10}$ cells/ml, or any range derivable therein. Cells may be manipulated subsequent to production, such as by concentrating them and/or reducing the cell culture volume.

In certain aspects, for large scale production of differentiated cells, the suspension culture may be moved at a speed of at least or about 5, 10, 15, 20, 30, 35, 40, 45, 50, 55, 60, 65, 70, 75, 80, 85, 90, 100 rpm, or any range of speed derivable therein. The movement may comprise stirring, shaking, or rotating as non-limiting examples.

The differentiation medium may comprise externally added fibroblast growth factor (FGF), hepatocyte growth factor or any differentiation factors to be used or screened. Such FGF may be at an amount of at least, about or at most 1, 5, 10, 15, 20, 25, 30, 35, 40, 45, 50, 55, 60, 65, 70, 75, 80, 90, 100, 150, 200 ng/ml or any range derivable therein. The aggregate formed from the pluripotent stem cells may be about, at least or at most 5, 10, 15, 20, 25, 30, 50, 100, 150, 200, 250, 300, 350, 400, 450, 500 μm in diameter. The diameter may be a mean, median or an average diameter.

The cardiac differentiation medium may also comprise externally adjusted fibroblast growth factor (FGF), hepatocyte growth factor (HGF) or any differentiation factors that are used or screened. Such FGF, HGF, or other differentiation factor like TGFβ signaling modulators may be at an amount of at least, about or at most 0.1, 1, 5, 10, 15, 20, 25, 30, 35, 40, 45, 50, 55, 60, 65, 70, 75, 80, 90, 100, 150, 200 ng/ml or any range derivable therein.

For selection or enrichment of desired cells, the pluripotent stem cells and/or progeny cells differentiated therefrom may contain one or more transgenes. For example, the one or more transgenes encode a selectable and/or screenable marker under the control of a lineage-specific promoter. The method may further comprise enriching or purifying the differentiated cells, e.g., based on marker expression. For example, any steps of the methods may be performed under conditions to select for transgenic cells.

In certain aspects, the population of transgenic iPS cells may be clonally derived from a single transgenic iPS cell. In a further aspect, there may be provided a cell population of at least or about $10^7$, $10^8$, $10^9$, or up to about $10^{10}$ cells (or any range derivable therein) comprising at least 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99% or 100% (or any range derivable therein) selected lineage of cells produced by the method described above, such as cardiomyocytes, hepatocytes, or neurons.

In certain further embodiments, methods involve pluripotent stem cells as starting material for differentiation, which could be embryonic stem (ES) cells, induced pluripotent stem cells, or embryonic stem cells derived by somatic cell nuclear transfer. In a certain aspect, the pluripotent stem cells may be clonally derived from a single pluripotent stem cell, may comprise a substantial portion of cells clonally derived from a single cell, or may be a pool of multiple populations of cells, wherein each population of cells is clonally derived from a single cell. An exemplary process for obtaining pluripotent stem cells from a single cell may comprise incubating a single pluripotent stem cell in medium comprising a ROCK inhibitor or a myosin II inhibitor (e.g., blebbistatin) under conditions to promote cell growth, such as being incubated under adherent culture conditions. Prior to growing the pluripotent stem cells in the suspension culture for aggregate formation, the single pluripotent stem cell as the originating source may be passaged once, twice, three times, four times, or preferably at least five times. In another aspect, the pluripotent stem cells may also be derived from an iPS cell population comprising more than a single cell.

In still further aspects, about $10^7$ to about $10^{10}$ of the pluripotent stem cells may be first incubated in the suspension culture for aggregate formation. The pluripotent stem cell aggregates may be formed by incubating pluripotent stem cells with aggregate promotion medium comprising a ROCK inhibitor or a myosin II inhibitor, which may be about 0.05 to about 5 μM, for example, at least or about 0.05, 0.1, 0.2, 0.5, 0.8, 1, 1.5, 2, 2.5, 5 μM, or any concentration effective for promoting cell growth or survival, including any range derivable therein.

In certain aspects, a culture medium, such as an aggregate promotion medium, may comprise fibroblast growth factor (FGF), for example at a concentration of about 5 to 200 ng/ml, such as at least or about 10, 15, 20, 25, 30, 35, 40, 45, 50, 55, 60, 65, 70, 75, 80, 85, 90, 95, 100, 150, 180, 200 ng/ml, or any range derivable therein. Optionally hepatic growth factor (HGF) may also be included, for example at a concentration of at least or about 25, 30, 35, 40, 45, 50, 55, 60, 65, 70, 75, 80, 85, 90, 95, 100, 150, 180, 200 ng/ml, or any range derivable therein.

The aggregate promotion medium may further comprise an antibiotic, such as zeocin, which may be used for cell enrichment or selection. The aggregates formed by pluripotent stem cells prior to differentiation may be at least or about 10, 20, 30, 40, 50, 60, 70, 80, 90, 100, 150, 200, 250, 300, 350, 400 μm (or any range derivable therein) in diameter; in another aspect, at least about 20%, 30%, 40%, 50%, 80%, 90%, 95%, or 99% (or any range derivable therein) of the aggregates may comprise at least or about 10, 15, 20, 25, 30, 35, 40, 45, 50, 80, 100, 150, 200, 250, 300, 400, 500, 1000 cells, or any range derivable therein. In certain aspects, a substantial portion (e.g., about more than 50%, 80%, 90%, 95%, 99% or any range derivable therein) of the aggregates are about 80 to 200 μm in diameter. The approximately uniformity of an optimal range of aggregate size may help differentiation as differentiation is guided by spatial cues and interaction between various cell types, which can be manipulated by varying aggregate size.

As in the step of cardiac differentiation, the suspension culture for differentiating the stem cells may comprise any differentiation medium suitable for differentiation, for example, a cardiac induction medium having FGF, which may have a concentration of about 5 to about 200 ng/ml, such as at least or about 10, 15, 20, 25, 30, 35, 40, 45, 50, 55, 60, 65, 70, 75, 80, 85, 90, 95, 100, 150, 180, 200 ng/ml or any range derivable therein. In a further aspect, the suspension culture for differentiating or the differentiation medium may not include added ROCK inhibitor.

Embodiments of the method may further comprise pooling multiple suspension cultures. For example, multiple suspension cultures of aggregated cells may be pooled prior to differentiating the stem cells, or multiple suspension cultures of differentiated stem cells, such as cardiomyocytes, may be pooled.

In some further aspects, the pluripotent stem cells, such as transgenic iPS cells, may contain one or more transgenes, such as transgenes encoding a selectable marker, which for example confers antibiotic resistance, or a screenable marker, which may be fluorescent or luminescent. The differentiation medium may comprise an antibiotic that allow for selection of cells expressing the transgene. For cell selection or enrichment, the transgene may be under the control of a tissue-specific promoter which is specific for the selected lineage.

Furthermore, in certain aspects, methods may further comprise enriching or purifying the differentiated cells. For cardiomyocyte differentiation, the pluripotent stem cell source or the cardiomyocytes differentiated therefrom may express one or more selectable or screenable transgene, wherein the transgene may be used for enrichment or purification of the cardiomyocytes. For example, the transgene may be an antibiotic resistance gene. For cardiomyocyte enrichment or isolation, such a transgene may be under the control of a promoter that is specific for cardiomyocytes, such as a myosin promoter or troponin T promoter.

Further embodiments provide an isolated cell population of at least or about $10^6$, $10^7$, $10^8$, $10^9$, $10^{10}$ cells (or any range derivable therein) comprising at least 90% (for example, at least or about 90%, 95%, 96%, 97%, 98%, 99%, 99.5%, or any range derivable therein) cells of the selected lineage. In a specific example, the cell population may contain a transgene under a promoter specific for cardiomyocytes, hepatocytes or neurons.

Embodiments discussed in the context of methods and/or compositions of the invention may be employed with respect to any other method or composition described herein. Thus, an embodiment pertaining to one method or composition may be applied to other methods and compositions of the invention as well.

As used herein the terms "encode" or "encoding" with reference to a nucleic acid are used to make the invention readily understandable by the skilled artisan; however, these terms may be used interchangeably with "comprise" or "comprising" respectively.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1C is actual data for 15 ml culture and FIG. 1D represents the calculated 1 L scale-up based on FIG. 1C data.

DESCRIPTION OF ILLUSTRATIVE EMBODIMENTS

I. Methods and Compositions

Figures 1A, 1B, 1C, 1D:
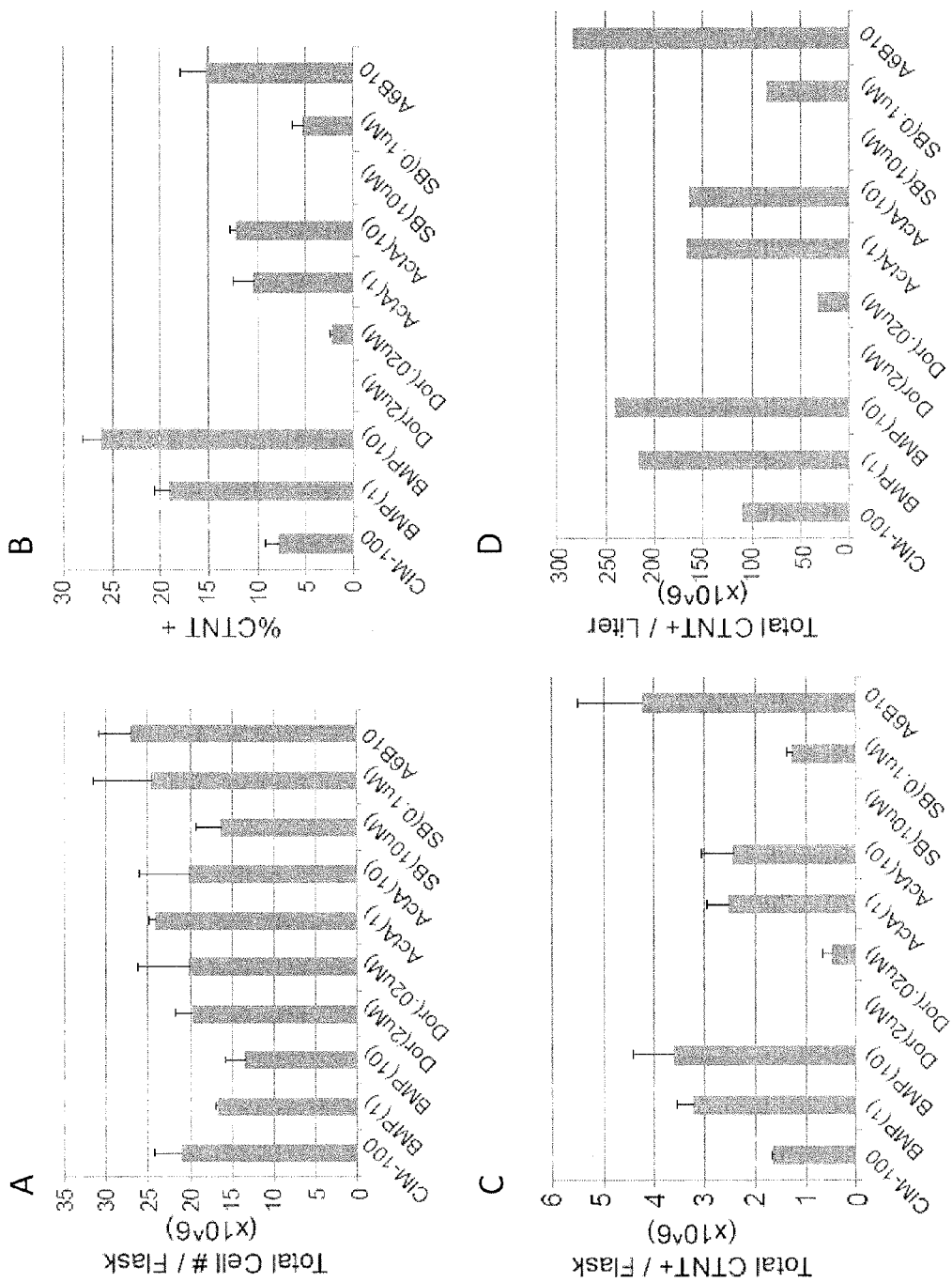
FIGS. 1A-1D: The results of a growth factor/inhibitor screen utilizing varying concentrations of BMP (1 ng/mL, 10 ng/mL), dorsomorphin (2 uM, 0.2 uM), Activin A (1 ng/mL, 10 ng/mL), SB-431542 (10 uM, 0.1 uM) and a combination of Activin A (6 ng/mL) and BMP4 (10 ng/mL).

A variety of different methods and compositions are described herein. Certain embodiments concern several important advantages that improve the stem cell differentiation process. It has been discovered that differentiation potential of pluripotent stem cells may be varied due to clone-to-clone variability of stem cells' endogenous signaling status and variability of culture medium. In some embodiments methods may be developed to increase uniformity and yields of the differentiated cells for a specific stem cell clone in a medium prepared from a selected batch of culture medium by screening of appropriate differentiation conditions. For example, the concentration and/or timing of addition of differentiation factors may be optimized. Further, provided herein is a method for determining the appropriate adjustments in growth factor additions that can be employed to dramatically improve cardiac differentiation for any given medium batch or pluripotent cell clone employed.

II. Definitions

"Pluripotency" refers to a stem cell that has the potential to differentiate into all cells constituting one or more tissues or organs, for example, any of the three germ layers: endoderm (interior stomach lining, gastrointestinal tract, the lungs), mesoderm (muscle, bone, blood, urogenital), or ectoderm (epidermal tissues and nervous system). "Pluripotent stem cells" used herein refer to cells that can differentiate into cells derived from any of the three germ layers, for example, descendants of totipotent cells or induced pluripotent cells.

"Induced pluripotent stem cells," commonly abbreviated as iPS cells or iPSCs, refer to a type of pluripotent stem cell artificially prepared from a non-pluripotent cell, typically an adult somatic cell, or terminally differentiated cell, such as fibroblast, a hematopoietic cell, a myocyte, a neuron, an epidermal cell, or the like, by introducing or contacting reprogramming factors.

"Embryonic stem (ES) cells" are pluripotent stem cells derived from early embryos.

"Suspension culture," refers to a culture in which cells, or aggregates of cells, multiply while suspended in liquid medium.

"Rho-associated kinase inhibitors," abbreviated as "ROCK inhibitors," refer to any substance that inhibits or reduces the function of Rho-associated kinase or its signaling pathway in a cell, such as a small molecule, an siRNA, a miRNA, an antisense RNA, or the like. "ROCK signaling pathway," as used herein, may include any signal processors involved in the ROCK-related signaling pathway, such as the Rho-ROCK-Myosin II signaling pathway, its upstream signaling pathway, or its downstream signaling pathway in a cell.

Examples of ROCK inhibitors include, but are not limited to, a Rho-specific inhibitor, a ROCK-specific inhibitor, a MRLC (myosin regulatory light chain)-specific inhibitor, or a Myosin II-specific inhibitor.

The term "aggregate promoting medium" means any medium that enhances the aggregate formation of stem cells without any restriction as to the mode of action.

The term "differentiation factor" means any agents that that modulates the differentiation of stem cells to a selected lineage without any restriction as to the mode of action. For example, the differentiation factors may be growth factors or any modulator of developmental pathway.

The term "differentiation medium" means any medium that enhances the differentiation of stem cells to a selected lineage without any restriction as to the mode of action. For example, the term "cardiac induction medium" or "cardiac differentiation medium" means any medium that enhances the differentiation of stem cells to cardiomyocytes without any restriction as to the mode of action.

The term "aggregates," i.e., embryoid bodies, refers to heterogeneous clusters comprising differentiated and partly differentiated cells that appear when pluripotent stem cells are allowed to differentiate in a non-specific fashion.

"Cardiomyocytes" refers generally to any cardiomyocytes lineage cells, and can be taken to apply to cells at any stage of cardiomyocytes ontogeny without any restriction, unless otherwise specified. For example, cardiomyocytes may include both cardiomyocyte precursor cells and mature cardiomyocytes.

"Hepatocytes" refers generally to any hepatocyte lineage cells, and can be taken to apply to cells at any stage of hepatocyte ontogeny without any restriction, unless otherwise specified. For example, hepatocytes may include both hepatocyte precursor cells and mature hepatocytes.

"Neurons" refers generally to any neuron lineage cells, and can be taken to apply to cells at any stage of neurons ontogeny without any restriction, unless otherwise specified. For example, neurons may include both neuron precursor cells and mature neurons.

A "gene," "polynucleotide," "coding region," "sequence," "segment," or "fragment," which "encodes" a particular protein, is a nucleic acid molecule which is transcribed and optionally also translated into a gene product, e.g., a polypeptide, in vitro or in vivo when placed under the control of appropriate regulatory sequences. The coding region may be present in either a cDNA, genomic DNA, or RNA form. When present in a DNA form, the nucleic acid molecule may be single-stranded (i.e., the sense strand) or double-stranded. The boundaries of a coding region are determined by a start codon at the 5' (amino) terminus and a translation stop codon at the 3' (carboxy) terminus. A gene can include, but is not limited to, cDNA from prokaryotic or eukaryotic mRNA, genomic DNA sequences from prokaryotic or eukaryotic DNA, and synthetic DNA sequences. A transcription termination sequence will usually be located 3' to the gene sequence.

The term "transgene," refers to a gene, nucleic acid, or polynucleotide which has been introduced into the cell or organism by artificial or natural means, such as an exogenous nucleic acid. An exogenous nucleic acid may be from a different organism or cell, or it may be one or more additional copies of a nucleic acid which occurs naturally within the organism or cell. By way of a non-limiting example, an exogenous nucleic acid is in a chromosomal location different from that of natural cells, or is otherwise flanked by a different nucleic acid sequence than that found in nature.

The term "promoter" is used herein in its ordinary sense to refer to a nucleotide region comprising a DNA regulatory sequence, wherein the regulatory sequence is derived from a gene which is capable of binding RNA polymerase and initiating transcription of a downstream (3' direction) coding sequence.

III. Sources of Pluripotent Stem Cells

Pluripotent stem cells may be used in present methods for differentiation along a selected lineage. However, different clones of pluripotent stem cells following the same differentiation protocol may have dramatically different differentiation outcome, probably due to the clone-to-clone variability of endogenous signaling status in the pluripotent stem cells. Methods and compositions have been disclosed in the present invention to address these issues by screening and using the optimal differentiation condition.

The term "pluripotent stem cell" refers to a cell capable of giving rise to cells of all three germinal layers, that is, endoderm, mesoderm and ectoderm. Although in theory a pluripotent stem cell can differentiate into any cell of the body, the experimental determination of pluripotency is typically based on differentiation of a pluripotent cell into several cell types of each germinal layer. In some embodiments of the present invention, a pluripotent stem cell is an embryonic stem (ES) cell derived from the inner cell mass of a blastocyst. In other embodiments, the pluripotent stem cell is an induced pluripotent stem cell derived by reprogramming somatic cells. In certain embodiments, the pluripotent stem cell is an embryonic stem cell derived by somatic cell nuclear transfer.

A. Embryonic Stem Cells

Embryonic stem (ES) cells are pluripotent cells derived from the inner cell mass of a blastocyst. ES cells can be isolated by removing the outer trophectoderm layer of a developing embryo, then culturing the inner mass cells on a feeder layer of non-growing cells. Under appropriate conditions, colonies of proliferating, undifferentiated ES cells are produced. The colonies can be removed, dissociated into individual cells, then replated on a fresh feeder layer. The replated cells can continue to proliferate, producing new colonies of undifferentiated ES cells. The new colonies can then be removed, dissociated, replated again and allowed to grow. This process of "subculturing" or "passaging" undifferentiated ES cells can be repeated a number of times to produce cell lines containing undifferentiated ES cells (U.S. Pat. Nos. 5,843,780; 6,200,806; 7,029,913). A "primary cell culture" is a culture of cells directly obtained from a tissue such as the inner cell mass of a blastocyst. A "subculture" is any culture derived from the primary cell culture.

Methods for obtaining mouse ES cells are well known. In one method, a preimplantation blastocyst from the 129 strain of mice is treated with mouse antiserum to remove the trophoectoderm, and the inner cell mass is cultured on a feeder cell layer of chemically inactivated mouse embryonic fibroblasts in medium containing fetal calf serum. Colonies of undifferentiated ES cells that develop are subcultured on mouse embryonic fibroblast feeder layers in the presence of fetal calf serum to produce populations of ES cells. In some methods, mouse ES cells can be grown in the absence of a feeder layer by adding the cytokine leukemia inhibitory factor (LIF) to serum-containing culture medium (Smith, 2000). In other methods, mouse ES cells can be grown in serum-free medium in the presence of bone morphogenetic protein and LIF (Ying et al., 2003).

Human ES cells can be obtained from blastocysts using previously described methods (Thomson et al., 1995; Thomson et al., 1998; Thomson and Marshall, 1998; Reubinoff et al, 2000.) In one method, day-5 human blastocysts are exposed to rabbit anti-human spleen cell antiserum, then exposed to a 1:5 dilution of Guinea pig complement to lyse trophectoderm cells. After removing the lysed trophectoderm cells from the intact inner cell mass, the inner cell mass is cultured on a feeder layer of gamma-inactivated mouse embryonic fibroblasts and in the presence of fetal bovine serum. After 9 to 15 days, clumps of cells derived from the inner cell mass can be chemically (i.e. exposed to trypsin) or mechanically dissociated and replated in fresh medium containing fetal bovine serum and a feeder layer of mouse embryonic fibroblasts. Upon further proliferation, colonies having undifferentiated morphology are selected by micropipette, mechanically dissociated into clumps, and replated (see U.S. Pat. No. 6,833,269). ES-like morphology is characterized as compact colonies with apparently high nucleus to cytoplasm ratio and prominent nucleoli. Resulting ES cells can be routinely passaged by brief trypsinization or by selection of individual colonies by micropipette. In some methods, human ES cells can be grown without serum by culturing the ES cells on a feeder layer of fibroblasts in the presence of basic fibroblast growth factor (Amit et al., 2000). In other methods, human ES cells can be grown without a feeder cell layer by culturing the cells on a protein matrix such as Matrigel™ or laminin in the presence of "conditioned" medium containing basic fibroblast growth factor (Xu et al., 2001). The medium is previously conditioned by coculturing with fibroblasts.

Methods for the isolation of rhesus monkey and common marmoset ES cells are also known (Thomson, and Marshall, 1998; Thomson et al., 1995; Thomson and Odorico, 2000).

Another source of ES cells are established ES cell lines. Various mouse cell lines and human ES cell lines are known and conditions for their growth and propagation have been defined. For example, the mouse CGR8 cell line was established from the inner cell mass of mouse strain 129 embryos, and cultures of CGR8 cells can be grown in the presence of LIF without feeder layers. As a further example, human ES cell lines H1, H7, H9, H13 and H14 were established by Thompson et al. In addition, subclones H9.1 and H9.2 of the H9 line have been developed. It is anticipated that virtually any ES or stem cell line known in the art and may be used with the present invention, such as, e.g., those described in Yu and Thompson, 2008, which is incorporated herein by reference.

The source of ES cells for use in connection with the present invention can be a blastocyst, cells derived from culturing the inner cell mass of a blastocyst, or cells obtained from cultures of established cell lines. Thus, as used herein, the term "ES cells" can refer to inner cell mass cells of a blastocyst, ES cells obtained from cultures of inner mass cells, and ES cells obtained from cultures of ES cell lines.

B. Induced Pluripotent Stem Cells

Induced pluripotent stem (iPS) cells are cells which have the characteristics of ES cells but are obtained by the reprogramming of differentiated somatic cells. Induced pluripotent stem cells have been obtained by various methods. In one method, adult human dermal fibroblasts are transfected with transcription factors Oct4, Sox2, c-Myc and Klf4 using retroviral transduction (Takahashi et al., 2007). The transfected cells are plated on SNL feeder cells (a mouse cell fibroblast cell line that produces LIF) in medium supplemented with basic fibroblast growth factor (bFGF). After approximately 25 days, colonies resembling human ES cell colonies appear in culture. The ES cell-like colonies are picked and expanded on feeder cells in the presence of bFGF.

Based on cell characteristics, cells of the ES cell-like colonies are induced pluripotent stem cells. The induced pluripotent stem cells are morphologically similar to human ES cells, and express various human ES cell markers. Also, when grown under conditions that are known to result in differentiation of human ES cells, the induced pluripotent stem cells differentiate accordingly. For example, the induced pluripotent stem cells can differentiate into cells having neuronal structures and neuronal markers. It is anticipated that virtually any iPS cells or cell lines may be used with the present invention, including, e.g., those described in Yu and Thompson, 2008.

In another method, human fetal or newborn fibroblasts are transfected with four genes, Oct4, Sox2, Nanog and Lin28 using lentivirus transduction (Yu et al., 2007). At 12-20 days post infection, colonies with human ES cell morphology become visible. The colonies are picked and expanded. The induced pluripotent stem cells making up the colonies are morphologically similar to human ES cells, express various human ES cell markers, and form teratomas having neural tissue, cartilage and gut epithelium after injection into mice.

Methods of preparing induced pluripotent stem cells from mouse are also known (Takahashi and Yamanaka, 2006). Induction of iPS cells typically require the expression of or exposure to at least one member from Sox family and at least one member from Oct family. Sox and Oct are thought to be central to the transcriptional regulatory hierarchy that specifies ES cell identity. For example, Sox may be Sox-1, Sox-2, Sox-3, Sox-15, or Sox-18; Oct may be Oct-4. Additional factors may increase the reprogramming efficiency, like Nanog, Lin28, Klf4, or c-Myc; specific sets of reprogramming factors may be a set comprising Sox-2, Oct-4, Nanog and, optionally, Lin-28; or comprising Sox-2, Oct4, Klf and, optionally, c-Myc.

IPS cells, like ES cells, have characteristic antigens that can be identified or confirmed by immunohistochemistry or flow cytometry, using antibodies for SSEA-1, SSEA-3 and SSEA-4 (Developmental Studies Hybridoma Bank, National Institute of Child Health and Human Development, Bethesda Md.), and TRA-1-60 and TRA-1-81 (Andrews et al., 1987). Pluripotency of embryonic stem cells can be confirmed by injecting approximately $0.5-10\times10^6$ cells into the rear leg muscles of 8-12 week old male SCID mice. Teratomas develop that demonstrate at least one cell type of each of the three germ layers.

In certain aspects of the present invention, iPS cells are made from reprogramming somatic cells using reprogramming factors comprising Oct family member and a Sox family member, such as Oct4 and Sox2 in combination with Klf or Nanog as describe above. The somatic cell in the present invention may be any somatic cell that can be induced to pluripotency, such as a fibroblast, a keratinocyte, a hematopoietic cell, a mesenchymal cell, a liver cell, a stomach cell, or a β cell. In a certain aspect, T cells may also be used as source of somatic cells for reprogramming (see U.S. Application No. 61/184,546, incorporated herein by reference).

Reprogramming factors may be expressed from expression cassettes comprised in one or more vectors, such as an integrating vector or an episomal vector, such as a EBV element-based system (see U.S. Application No. 61/058,858, incorporated herein by reference; Yu et al., 2009). In a further aspect, reprogramming proteins could be introduced directly into somatic cells by protein transduction (see U.S. Application No. 61/172,079, incorporated herein by reference).

C. Embryonic Stem Cells Derived by Somatic Cell Nuclear Transfer

Pluripotent stem cells can be prepared by means of somatic cell nuclear transfer, in which a donor nucleus is transferred into a spindle-free oocyte. Stem cells produced by nuclear transfer are genetically identical to the donor nuclei. In one method, donor fibroblast nuclei from skin fibroblasts of a rhesus macaque are introduced into the cytoplasm of spindle-free, mature metaphase II rhesus macaque ooctyes by electrofusion (Byrne et al., 2007). The fused oocytes are activated by exposure to ionomycin, then incubated until the blastocyst stage. The inner cell mass of selected blastocysts are then cultured to produce embryonic stem cell lines. The embryonic stem cell lines show normal ES cell morphology, express various ES cell markers, and differentiate into multiple cell types both in vitro and in vivo. As used herein, the term "ES cells" refers to embryonic stem cells derived from embryos containing fertilized nuclei. ES cells are distinguished from embryonic stem cells produced by nuclear transfer, which are referred to as "embryonic stem cells derived by somatic cell nuclear transfer."

IV. Culturing and Differentiation of Pluripotent Stem Cells

Depending on culture conditions, pluripotent stem cells can produce colonies of differentiated cells or undifferentiated cells. For improved differentiation consistency and efficiency, methods involving determination of appropriate growth factors conditions for differentiation of a selected pluripotent stem cell clone in a selected batch of culture medium may be provided, as well as use of the determined appropriate condition for differentiation of cells from the same stem cell clone in the selected batch of culture medium.

The term "differentiate" means the progression of a cell down a developmental pathway. The term "differentiated" is a relative term describing a cell's progression down a developmental pathway in comparison with another cell. For example, a pluripotent cell can give rise to any cell of the body, while a more differentiated cell such as a hematopoetic cell will give rise to fewer cell types.

Cultures of pluripotent stem cells are described as "undifferentiated" when a substantial proportion of stem cells and their derivatives in the population display morphological characteristics of undifferentiated cells, clearly distinguishing them from differentiated cells of embryo or adult origin. Undifferentiated ES or iPS cells are recognized by those skilled in the art, and typically appear in the two dimensions of a microscopic view in colonies of cells with high nuclear/cytoplasmic ratios and prominent nucleoli. It is understood that colonies of undifferentiated cells can have neighboring cells that are differentiated.

In certain aspects, starting cells for the present methods may comprise at least or about $10^4$, $10^5$, $10^6$, $10^7$, $10^8$, $10^9$, $10^{10}$, $10^{11}$, $10^{12}$, $10^{13}$ cells or any range derivable therein. The starting cell population may have a seeding density of at least or about 10, $10^1$, $10^2$, $10^3$, $10^4$, $10^5$, $10^6$, $10^7$, $10^8$ cells/ml, or any range derivable therein.

A. Medium for Adjustments in Differentiation Factor Conditions

The culturing conditions according to certain aspects of the present invention may be determined depending on the medium and stem cells used. The method disclosed herein may overcome variability in different batches of culture medium even of the same type. For example, a group of test medium may be prepared from the same batch of culture medium by addition of various amounts of differentiation factors at a defined or varied test period and testing differentiation efficiency of a selected stem cell clone in the variable test media, therefore determining the optimal condition for the selected batch of culture medium to differentiate the selected pluripotent stem cell clone.

The medium according to certain aspects of the present invention can be prepared using a medium to be used for culturing animal cells as its basal medium. As the basal medium, any of TeSR, BME, BGJb, CMRL 1066, Glasgow MEM, Improved MEM Zinc Option, IMDM, Medium 199, Eagle MEM, αMEM, DMEM, Ham, RPMI 1640, and Fischer's media, as well as any combinations thereof can be used, but the medium is not particularly limited thereto as far as it can be used for culturing animal cells. Different batches of the same medium may be variable in terms of stem cell differentiation due to difference in activity of recombination proteins or components or alternatives of serum. Therefore, methods of certain aspects of the invention are provided to account for this variability.

The medium can be a serum-containing or serum-free medium. The serum-free medium refers to media with no unprocessed or unpurified serum and accordingly, can include media with purified blood-derived components or animal tissue-derived components (such as growth factors). From the aspect of preventing contamination with heterogeneous animal-derived components, serum can be derived from the same animal as that of the stem cell(s).

The medium may contain or may not contain any alternatives to serum. The alternatives to serum can include materials which appropriately contain albumin (such as lipid-rich albumin, albumin substitutes such as recombinant albumin, plant starch, dextrans and protein hydrolysates), transferrin (or other iron transporters), fatty acids, insulin, collagen precursors, trace elements, 2-mercaptoethanol, 3'-thiolglycerol, or equivalents thereto. The alternatives to serum can be prepared by the method disclosed in International Publication No. 98/30679, for example. Alternatively, any commercially available materials can be used for more convenience. The commercially available materials include knockout Serum Replacement (KSR), Chemically-defined Lipid concentrated (Gibco), and Glutamax (Gibco).

The medium can also contain fatty acids or lipids, amino acids (such as non-essential amino acids), vitamin(s), growth factors, cytokines, antioxidant substances, 2-mercaptoethanol, pyruvic acid, buffering agents, and inorganic salts. The concentration of 2-mercaptoethanol can be, for example, about 0.05 to 1.0 mM, and particularly about 0.1 to 0.5 mM, but the concentration is particularly not limited thereto as long as it is appropriate for culturing the stem cell(s).

B. Culture Conditions

A culture vessel used for culturing the stem cell(s) can include, but is particularly not limited to: flask, flask for tissue culture, dish, petri dish, dish for tissue culture, multi dish, micro plate, micro-well plate, multi plate, multi-well plate, micro slide, chamber slide, tube, tray, CellSTACK® Chambers, culture bag, and roller bottle, as long as it is capable of culturing the stem cells therein. The stem cells may be cultured in a volume of at least or about 0.2, 0.5, 1, 2, 5, 10, 20, 30, 40, 50 ml, 100 ml, 150 ml, 200 ml, 250 ml, 300 ml, 350 ml, 400 ml, 450 ml, 500 ml, 550 ml, 600 ml, 800 ml, 1000 ml, 1500 ml, or any range derivable therein, depending on the needs of the culture. In a certain embodiment, the culture vessel may be a bioreactor, which may refer to any device or system that supports a biologically active environment. The bioreactor may have a volume of at least or about 2, 4, 5, 6, 8, 10, 15, 20, 25, 50, 75, 100, 150, 200, 500 liters, 1, 2, 4, 6, 8, 10, 15 cubic meters, or any range derivable therein.

The culture vessel can be cellular adhesive or non-adhesive and selected depending on the purpose. The cellular adhesive culture vessel can be coated with any of substrates for cell adhesion such as extracellular matrix (ECM) to improve the adhesiveness of the vessel surface to the cells. The substrate for cell adhesion can be any material intended to attach stem cells or feeder cells (if used). The substrate for cell adhesion includes collagen, gelatin, poly-L-lysine, poly-D-lysine, laminin, and fibronectin and mixtures thereof for example Matrigel™, and lysed cell membrane preparations (Klimanskaya et al., 2005).

Other culturing conditions can be appropriately defined. For example, the culturing temperature can be about 30 to 40° C., for example, at least or about 31, 32, 33, 34, 35, 36, 37, 38, 39° C. but particularly not limited to them. The $CO_2$ concentration can be about 1 to 10%, for example, about 2 to 5%, or any range derivable therein. The oxygen tension can be at least or about 1, 5, 8, 10, 20%, or any range derivable therein.

The methods of the present invention can be used for adhesion culture of stem cells, for example. In this case, the cells can be cultured in the presence of feeder cells. In the case where the feeder cells are used in the methods of the present invention, stromal cells such as fetal fibroblasts can be used as feeder cells (for example, refer to; Manipulating the Mouse Embryo A Laboratory Manual (1994); Gene Targeting, A Practical Approach (1993); Martin (1981); Evans et al. (1981); Jainchill et al., (1969); Nakano et al., Science (1996); Kodama et al. (1982); and International Publication Nos. 01/088100 and 2005/080554).

The methods of the present invention can be also used for a suspension culture of stem cells, including suspension culture on carriers (Fernandes et al., 2007) or gel/biopolymer encapsulation (United States Patent Publication No. 2007/0116680). The term suspension culture of the stem cells means that the stem cells are cultured under non-adherent condition with respect to the culture vessel or feeder cells (if used) in a medium. The suspension culture of stem cells includes a dissociation culture of stem cells and an aggregate suspension culture of stem cells. The term dissociation culture of stem cells means that suspended stem cells is cultured, and the dissociation culture of stem cells include those of single stem cell or those of small cell aggregates composed of a plurality of stem cells (for example, about 2 to 400 cells). When the aforementioned dissociation culture is continued, the cultured, dissociated cells form a larger aggregate of stem cells, and thereafter an aggregate suspension culture can be performed. The aggregate suspension culture includes an embryoid culture method (see Keller et al., 1995), and a SFEB method (Watanabe et al., 2005); International Publication No. 2005/123902).

C. Culturing of Pluripotent Stem Cells

Pluripotent stem cells can be maintained in an undifferentiated state by culturing the cells in the presence of serum and a feeder layer, such as a feeder layer of mouse embryonic fibroblasts. Other methods for maintaining stem cells in an undifferentiated state are also known. For example, mouse ES cells can be maintained in an undifferentiated state by culturing in the presence of LIF without a feeder layer. However, unlike mouse ES cells, human ES cells do not respond to LIF. Human ES cells can be maintained in an undifferentiated state by culturing ES cells on a feeder layer of fibroblasts in the presence of basic fibroblast growth factor (Amit et al., 2000), or by culturing on a protein matrix, such as Matrigel™ or laminin, without a feeder layer and in the presence of fibroblast-conditioned medium plus basic fibroblast growth factor (Xu et al., 2001; U.S. Pat. No. 6,833,269).

Methods for preparing and culturing pluripotent stem cells such as ES cells can be found in standard textbooks and reviews in cell biology, tissue culture, and embryology, including teratocarcinomas and embryonic stem cells: A practical approach (1987); Guide to Techniques in Mouse Development (1993); Embryonic Stem Cell Differentiation in vitro (1993); Properties and uses of Embryonic Stem Cells: Prospects for Application to Human Biology and Gene Therapy (1998), all incorporated herein by reference. Standard methods used in tissue culture generally are described in Animal Cell Culture (1987); Gene Transfer Vectors for Mammalian Cells (1987); and Current Protocols in Molecular Biology and Short Protocols in Molecular Biology (1987 & 1995).

After somatic cells are introduced or contacted with reprogramming factors, these cells may be cultured in a medium sufficient to maintain the pluripotency and the undifferentiated state. Culturing of induced pluripotent stem (iPS) cells can use various medium and techniques developed to culture primate pluripotent stem cells, more specially, embryonic stem cells, as described in U.S. Pat. Publication 2007/0238170 and U.S. Pat. Publication 2003/0211603, and U.S. Pat. Publication 2008/0171385, which are hereby incorporated by reference. It is appreciated that additional methods for the culture and maintenance of pluripotent stem cells, as would be known to one of skill, may be used with the present invention.

In certain embodiments, undefined conditions may be used; for example, pluripotent cells may be cultured on fibroblast feeder cells or a medium that has been exposed to fibroblast feeder cells in order to maintain the stem cells in an undifferentiated state. Alternately, pluripotent cells may be cultured and maintained in an essentially undifferentiated state using defined, feeder-independent culture system, such as a TeSR medium (Ludwig et al., 2006a; Ludwig et al., 2006b). Feeder-independent culture systems and media may be used to culture and maintain pluripotent cells. These approaches allow human pluripotent stem cells to remain in an essentially undifferentiated state without the need for mouse fibroblast "feeder layers." As described herein, various modifications may be made to these methods in order to reduce costs as desired.

Various matrix components may be used in culturing and maintaining human pluripotent stem cells. For example, collagen IV, fibronectin, laminin, and vitronectin in combination may be used to coat a culturing surface as a means of providing a solid support for pluripotent cell growth, as described in Ludwig et al. (2006a; 2006b), which are incorporated by reference in their entirety.

Matrigel™ may also be used to provide a substrate for cell culture and maintenance of human pluripotent stem cells. Matrigel™ is a gelatinous protein mixture secreted by mouse tumor cells and is commercially available from BD Biosciences (New Jersey, USA). This mixture resembles the complex extracellular environment found in many tissues and is used by cell biologists as a substrate for cell culture.

D. ROCK Inhibitors and Myosin II inhibitors

Pluripotent stem cells, especially human ES cells and iPS cells, are vulnerable to apoptosis upon cellular detachment and dissociation, which are important for clonal isolation or expansion and differentiation induction. For deriving a stem cell clone for differentiation, ROCK inhibitors or myosin II inhibitors may be used to increase clonal efficiency.

Recently, a small class of molecules have been found to increase clonal efficiency and survival of dissociated pluripotent stem cells, such as Rho-associated kinase (ROCK) inhibitors, which are inhibitors for ROCK-related signaling pathways, for example, Rho-specific inhibitors, ROCK-specific inhibitors or myosin II-specific inhibitors. In certain aspects of the invention, ROCK inhibitors may be used for culturing and passaging of pluripotent stem cells and/or differentiation of the stem cells. Therefore, ROCK inhibitors could be present in any cell culture medium in which pluripotent stem cells grow, dissociate, form aggregates, or undergo differentiation, such as an adherent culture or suspension culture.

ROCK signaling pathways may include Rho family GTPases, ROCK, a major effector kinase downstream of Rho, Myosin II, the predominant effector downstream of ROCK (Harb et al., 2008), and any intermediate, upstream, or downstream signal processors. ROCK may phosphorylate and inactivate myosin phosphatase target subunit 1 (MYPT1), one of the major downstream targets of ROCK that negatively regulates myosin function through dephosphorylation of myosin regulatory light chain (MRLC).

Rho-specific inhibitors, such as *Clostridium botulinum* C3 exoenzyme, and/or Myosin II-specific inhibitors may also be used as a ROCK inhibitor in certain aspects of the invention. Unless otherwise stated herein, myosin II inhibitors, such as blebbistatin, can substitute for the experimental use of ROCK inhibitors.

Myosin II was first studied for its role in muscle contraction, but it functions also in non-muscle cells. Myosin II (also known as conventional myosin) contains two heavy chains, each about 2000 amino acids in length, which constitute the head and tail domains. Each of these heavy chains contains the N-terminal head domain, while the C-terminal tails take on a coiled-coil morphology, holding the two heavy chains together (imagine two snakes wrapped around each other, such as in a caduceus). Thus, myosin II has two heads. It also contains 4 light chains (2 per head), which bind the heavy chains in the "neck" region between the head and tail. These light chains are often referred to as the essential light chain and the regulatory light chain. An exemplary Myosin II-specific inhibitor may be Blebbistatin or it derivatives.

ROCKs are serine/threonine kinases that serve as a target proteins for Rho (of which three isoforms exist—RhoA, RhoB and RhoC). Theses kinases were initially characterized as mediators of the formation of RhoA-induced stress fibers and focal adhesions. The two ROCK isoforms—ROCK1 (p160ROCK, also called ROKβ) and ROCK2 (ROKα)—are comprised of a N-terminal kinase domain, followed by a coiled-coil domain containing a Rho-binding domain and a pleckstrin-homology domain (PH). Both ROCKs are cytoskeletal regulators, mediating RhoA effects on stress fiber formation, smooth muscle contraction, cell adhesion, membrane ruffling and cell motility. ROCKs may exert their biological activity by targeting downstream molecules, such as myosin II, myosin light chain (MLC), MLC phosphatase (MLCP) and the phosphatase and tensin homolog (PTEN).

An exemplary ROCK-specific inhibitor is Y-27632, which selectively targets ROCK1 (but also inhibits ROCK2), as well as inhibits TNF-α and IL-1β. It is cell permeable and inhibits ROCK1/ROCK2 ($IC_{50}$=800 nM) by competing with ATP. Ishizaki et al. (2000), incorporated herein by reference as if set forth in its entirety. Other ROCK inhibitors include, e.g., H-1152, Y-30141, Wf-536, HA-1077, hydroxyl-HA-1077, GSK269962A and SB-772077—B. Doe et al. (2007); Ishizaki et al., supra; Nakajima et al. (2003); and Sasaki et al. (2002), each of which is incorporated herein by reference as if set forth in its entirety.

Other non-limiting examples of ROCK inhibitors include H-1152 and Fasudil (also referred to as HA1077), Y-30141 (described in U.S. Pat. No. 5,478,838), and derivatives thereof, and antisense nucleic acid for ROCK, RNA interference inducing nucleic acid (for example, siRNA), competitive peptides, antagonist peptides, inhibitory antibodies, antibody-ScFV fragments, dominant negative variants and expression vectors thereof. Further, since other low molecular compounds are known as ROCK inhibitors, such compounds or derivatives thereof can be also used in embodiments (for example, refer to U.S. Patent Publication Nos. 20050209261, 20050192304, 20040014755, 20040002508, 20040002507, 20030125344 and 20030087919, and International Patent Publication Nos. 2003/062227, 2003/059913, 2003/062225, 2002/076976 and 2004/039796, which are hereby incorporated by reference). In the present invention, a combination of one or two or more of the ROCK inhibitors can also be used.

According to some embodiments, the stem cell can be treated with a ROCK inhibitor or myosin II inhibitor in a medium. Thereby, the medium used in the methods of the present invention may already contain the ROCK inhibitor or Myosin II inhibitor or alternatively, the methods of the present invention may involve a step of adding the ROCK inhibitor or myosin II inhibitor to the medium. The concentration of the ROCK inhibitor or myosin II inhibitor in the medium is particularly not limited as far as it can achieve the desired effects such as the improved survival rate of stem cells. A ROCK inhibitor or myosin II inhibitor, e.g., Y-27632, HA-1077, H-1152, or blebbistatin, may be used at an effective concentration of at least or about 0.02, 0.05, 0.1, 0.2, 0.5, 1, 2, 3, 4, 5, 10, 15, 20, 25, 30, 35, 40, 45, 50, 100, 150, 200, 500 to about 1000 μM, or any range derivable therein. These amounts may refer to an amount of a ROCK inhibitor or myosin II inhibitor individually or in combination with one or more ROCK inhibitors or myosin II inhibitors.

The time for treating with the ROCK inhibitor or myosin II inhibitor is particularly not limited as long as it is a time duration for which the desired effects such as the improved survival rate of stem cells can be achieved. For example, when the stem cell is a pluripotent stem cells such as a human embryonic stem cell, the time for treating is at least or about 10, 15, 20, 25, 30 minutes to several hours (e.g., at least or about one hour, two hours, three hours, four hours, five hours, six hours, eight hours, 12 hours, 16 hours, 24 hours, 36 hours, 48 hours, or any range derivable therein) before dissociation. After dissociation, the pluripotent stem cell can be treated with the ROCK inhibitor or myosin II inhibitor for, for example, at least or about 2, 3, 4, 5, 6, 7, 8, 9, 10, 11, 12, 16, 24, 48 hours or more to achieve the desired effects.

The density of the stem cell(s) to be treated with the ROCK inhibitor or myosin II inhibitor is particularly not limited as far as it is a density at which the desired effects such as the improved survival rate of stem cells can be achieved. It is, for example, about $1.0 \times 10^1$ to $1.0 \times 10^7$ cells/ml, more particularly about $1.0 \times 10^2$ to $1.0 \times 10^7$ cells/ml, further more particularly about $1.0 \times 10^3$ to $1.0 \times 10^7$ cells/ml, and most particularly about $3.0 \times 10^4$ to $2.0 \times 10^6$ cells/ml.

In certain embodiments, stem cells are cultured in the presence of ROCK inhibitors or myosin II inhibitors to improve survival at low density (dissociated into single cells or small aggregates), cloning efficiency or passaging efficiency. In certain embodiments of the invention, the stem cells are cultured in the absence of feeder cells, feeder cell extracts and/or serum. The stem cells can be cultured in the presence of a ROCK inhibitor or myosin II inhibitor prior to subcloning or passaging, e.g., for at least one hour before subcloning or passaging. Alternatively or additionally, the stem cells are maintained in the presence of a ROCK inhibitor or myosin II inhibitor during or after subcloning or passaging.

In certain embodiments, the stem cells are maintained in the presence of a ROCK inhibitor or myosin II inhibitor for at most or at least about 4, 8, 12 hours, about 2, about 4, or about 6 days, or any range derivable therein. In other embodiments, the stem cells are maintained in the presence of a ROCK inhibitor or myosin II inhibitor for at least one to five passages. Optionally, the ROCK inhibitor or myosin II inhibitor is subsequently withdrawn from the culture medium, for example after about 4, 8, 12 hours or after about 2, about 4, or about 6 days, or any range derivable therein. In other embodiments, the ROCK inhibitor or myosin II inhibitor is withdrawn after at least one, two, three, four, five passages or more, or any range derivable therein.

The stem cells to be treated with a ROCK inhibitor or myosin II inhibitor can be dissociated cells or non-dissociated cells. The dissociated cells refer to cells treated to promote cell dissociation (for example, the dissociation described later). Dissociated cells include a single cell and cells having formed a small cell clump (aggregate) of several (typically about 2 to 50, 2 to 20, or 2 to 10) cells. The dissociated cells can be suspended (floating) cells or adhered cells. For example, it has been known that ES cells such as human ES cells are susceptible to specific conditions such as dissociation (and/or suspension culture after dissociation). The methods of the present invention have particular use when the stem cell is subject to conditions at which hitherto cell death would have occurred.

Certain aspects of the present invention can further involve a step of dissociating stem cells. Stem cell dissociation can be performed using any known procedures. These procedures include treatments with a chelating agent (such as EDTA), an enzyme (such as trypsin, collagenase), or the like, and operations such as mechanical dissociation (such as pipetting). The stem cell(s) can be treated with the ROCK inhibitor or myosin II inhibitor before and/or after dissociation. For example, the stem cell(s) can be treated only after dissociation.

E. Single Cell Passaging

In some embodiments of pluripotent stem cell culturing, once a culture container is full, the colony is split into aggregated cells or even single cells by any method suitable for dissociation, which cell are then placed into new culture containers for passaging. Cell passaging or splitting is a technique that enables to keep cells alive and growing under cultured conditions for extended periods of time. Cells usually would be passed when they are about 70%-100% confluent.

Single-cell dissociation of pluripotent stem cells followed by single cell passaging may be used in the present methods with several advantages, like facilitating cell expansion, cell sorting, and defined seeding for differentiation and enabling automatization of culture procedures and clonal expansion. For example, progeny cell clonally derivable from a single cell may be homogenous in genetic structure and/or synchronized in cell cycle, which may increase targeted differentiation. Exemplary methods for single cell passaging may be as described in U.S. Pat. App. 2008/0171385, which is incorporated herein by reference.

In certain embodiments, pluripotent stem cells may be dissociated into single individual cells, or a combination of single individual cells and small cell clusters comprising 2, 3, 4, 5, 6, 7, 8, 9, 10 cells or more. The dissociation may be achieved by mechanical force, or by a cell dissociation agent, such as NaCitrate, or an enzyme, for example, trypsin, trypsin-EDTA, TrypLE Select, or the like.

Based on the source of pluripotent stem cells and the need for expansion, the dissociated cells may be transferred individually or in small clusters to new culture containers in a splitting ratio such as at least or about 1:2, 1:4, 1:5, 1:6, 1:8, 1:10, 1:20, 1:40, 1:50, 1:100, 1:150, 1:200, or any range derivable therein. Suspension cell line split ratios may be done on volume of culture cell suspension. The passage interval may be at least or about every 1, 2, 3, 4, 5, 6, 7, 8, 9, 10, 11, 12, 13, 14, 15, 16, 17, 18, 19, 20 days or any range derivable therein. For example, the achievable split ratios for the different enzymatic passaging protocols may be 1:2 every 3-7 days, 1:3 every 4-7 days, and 1:5 to 1:10 approximately every 7 days, 1:50 to 1:100 every 7 days. When high split ratios are used, the passage interval may be extended to at least 12-14 days or any time period without cell loss due to excessive spontaneous differentiation or cell death.

In certain aspects, single cell passaging may be in the presence of a small molecule effective for increasing cloning efficiency and cell survival, such as a ROCK inhibitor as described above. Such a ROCK inhibitor or myosin II inhibitor, e.g., Y-27632, HA-1077, H-1152, or blebbistatin, may be used at an effective concentration, for example, at least or about 0.02, 0.05, 0.1, 0.2, 0.5, 1, 2, 3, 4, 5, 10, 15, 20, 25, 30, 35, 40, 45, 50 to about 100 µM, or any range derivable therein.

F. Differentiation of Stem Cells

Differentiation of pluripotent stem cells can be induced in a variety of manners, such as in attached colonies or by formation of cell aggregates, e.g., in low-attachment environment, wherein those aggregates are referred to as embryoid bodies (EBs). The molecular and cellular morphogenic signals and events within EBs mimic many aspects of the natural ontogeny of such cells in a developing embryo. However, currently there remain no satisfactory methods for producing selected lineage cells in a consistent manner. Certain aspects of the invention disclose methods using previously determined differentiation condition for differentiation of stem cells to overcome the variability among different stem cell clones and culture media batches.

Embryoid bodies (EBs) are aggregates of cells derived from pluripotent stem cells, such as ES cells or iPS cells, and have been studied for years with mouse embryonic stem cells. In order to recapitulate some of the cues inherent to in vivo differentiation, certain aspects of the invention may employ three-dimensional aggregates (i.e., embryoid bodies) as an intermediate step. Upon aggregation, differentiation is initiated and the cells begin to a limited extent to recapitulate embryonic development. Though they cannot form trophectodermal tissue (which includes the placenta), cells of virtually every other type present in the organism can develop. The present invention may further promote cardiac differentiation following aggregate formation.

Cell aggregation may be imposed by hanging drop, plating upon non-tissue culture treated plates or spinner flasks; either method prevents cells from adhering to a surface to form the typical colony growth. As described above, ROCK inhibitors or myosin II inhibitors may be used before, during or after aggregate formation to culture pluripotent stem cells.

Pluripotent stem cells may be seeded into aggregate promotion medium using any method known in the art of cell culture. For example, pluripotent stem cells may be seeded as a single colony or clonal group into aggregate promotion medium, and pluripotent stem cells may also be seeded as essentially individual cells. In some embodiments, pluripotent stem cells are dissociated into essentially individual cells using mechanical or enzymatic methods known in the art. By way of non-limiting example, pluripotent stem cells may be exposed to a proteolytic enzyme which disrupts the connections between cells and the culturing surface and between the cells themselves. Enzymes which may be used to individualize pluripotent stem cells for aggregate formation and differentiation may include, but are not limited to, trypsin, in its various commercial formulations, such as TrypIE, or a mixture of enzymes such as Accutase®.

In certain embodiments, pluripotent cells may be added or seeded as essentially individual (or dispersed) cells to a culturing medium for culture formation on a culture surface. The culturing medium into which cells are seeded may comprise TeSR medium or mTeSR medium added with a predetermined optimal condition of differentiation factors tailed to the culture medium and selected pluripotent stem cell clone.

For example, dispersed pluripotent cells are seeded into a culturing medium at a density of from about $10^4$ cells/ml to about $10^{10}$ cells/ml. More particularly, pluripotent cells are seeded at a density of from about $10^5$ cells/ml to about $10^7$ cells/ml, or about $0.5 \times 10^6$ cells/ml to about $3 \times 10^6$ cells/ml. In these embodiments, a culturing surface may be comprised of essentially any material which is compatible with standard aseptic cell culture methods in the art, for example, a non-adherent surface. A culturing surface may additionally comprise a matrix component as described herein. In certain embodiments, a matrix component may be applied to a culturing surface before contacting the surface with cells and medium.

V. Differentiation Factors

In certain aspects of the invention, the timing and amount of addition of differentiation factors may be screened for appropriate conditions for differentiation of stem cells into a selected cell lineage. In a particular aspect, the differentiation factors may be growth factors that are involved in cell development. The differentiation factors may include, but not be limited to, one or more of modulators of signaling pathways of bone morphogenetic protein, ActivinA/Nodal, vascular endothelial growth factor (VEGF), dickkopf homolog 1 (DKK1), basic fibroblast growth factor (bFGF), insulin growth factor (IGF), and/or epidermal growth factor (EGF).

It is contemplated that additional factors may be screened for its optimal concentration or timing in the cell differentiation environment, including, but not limited to, fibronectin, laminin, heparin, heparin sulfate, retinoic acid, members of the epidermal growth factor family (EGFs), members of the fibroblast growth factor family (FGFs) including FGF2, FGF7, FGF8, and/or FGF10, members of the platelet derived growth factor family (PDGFs), transforming growth factor (TGF)/bone morphogenetic protein (BMP)/growth and differentiation factor (GDF) factor family agonists or antagonists including but not limited to noggin, follistatin, chordin, gremlin, cerberus/DAN family proteins, GDF family proteins such as GDF-3, ventropin, and amnionless or variants or functional fragments thereof TGF/BMP/GDF antagonists could also be added in the form of TGF/BMP/GDF receptor-Fc chimeras. Other factors that may be screened include molecules that can activate or inactivate signaling through Notch receptor family, including but not limited to proteins of the Delta-like and Jagged families as well as inhibitors of Notch processing or cleavage, or variants or functional fragments thereof. Other growth factors may include members of the insulin like growth factor family (IGF), insulin, the wingless related (WNT) factor family, and the hedgehog factor family or variants or functional fragments thereof. Additional factors may be screened or added to promote mesoderm stem/progenitor, endoderm stem/progenitor, mesoderm stem/progenitor, or definitive endoderm stem/progenitor proliferation and survival as well as survival and differentiation of derivatives of these progenitors.

Without wishing to be bound by theory, in certain aspects it is contemplated that TGFβ signaling pathways may be delicately regulated by adjusting timing and level of the external addition of certain growth factors to achieve optimal specific lineage differentiation condition, such as for differentiation of cardiomyocytes, neurons or hepatocytes. In certain aspects, the addition of differentiation factors may help account for variability in the activity of TGFβ signaling pathway activity for a combination of a selected stem cell clone and a selected culture medium, particularly, in the relative activity of different TGFβ signaling pathways, such as a relative activity ratio between BMP signaling and Activin signaling.

The transforming growth factor beta (TGFβ) signaling pathway is involved in many cellular processes in both the adult organism and the developing embryo including cell growth, cell differentiation, apoptosis, cellular homeostasis and other cellular functions. In spite of the wide range of cellular processes that the TGFβ signaling pathway regulates, the process is relatively simple. TGFβ superfamily ligands bind to a type II receptor, which recruits and phosphorylates a type I receptor. The type I receptor then phosphorylates receptor-regulated SMADs (R-SMADs) which can now bind the coSMAD SMAD4. R-SMAD/coSMAD complexes accumulate in the nucleus where they act as transcription factors and participate in the regulation of target gene expression.

Stem cells exhibit self-renewing capacity and pluripotency in generating the multitude of embryonic and adult cell types of the metazoan body (reviewed by Rossi et al., 2008). Growth factors, such as TGFβ and FGF, regulate stem cell self-renewal and differentiation. FGF2, the most widely used growth factor that supports mouse and human embryonic stem cell (ESC) self-renewal in culture, induces TGFβ/activin ligands and receptors while suppressing BMP-like activities (Greber et al., 2007; Ogawa et al., 2007). Furthermore, pharmacological inhibitors of the TGFβ/nodal type I receptor family suppress human and mouse ESC self-renewal (Ogawa et al., 2007). In general, TGFβ inhibits differentiation of pluripotent progenitor cells, whereas BMP induces their differentiation (Watabe and Miyazono, 2009).

To promote self-renewal of ESCs, TGFβ/nodal signaling activates SMAD2 and SMAD3, which directly induce Nanog, one of the crucial stem cell transcription factors (Xu, R. H. et al., 2008). TGFβ and FGF signaling synergize by enhancing binding of Smad complexes to the Nanog promoter. Interestingly, NANOG provides a molecular link for the antagonism between TGFβ (the self-renewing factor) and BMP (the differentiation factor) in ESCs. Nanog binds to SMAD1, inhibiting its transcriptional activity and limiting the BMP signaling potential that promotes early mesodermal differentiation or tissue-specific differentiation later in development (Suzuki et al., 2006). This example is likely to be expanded to additional regulators of ESC self renewal and differentiation as a result of genome-wide screens for the transcription and signaling factors of these pathways (Chen et al., 2008).

The TGF Beta superfamily of ligands include: Bone morphogenetic proteins (BMPs), Growth and differentiation factors (GDFs), Anti-müllerian hormone (AMH), Activin, Nodal and TGFβ's. Signaling begins with the binding of a TGF beta superfamily ligand to a TGF beta type II receptor. The type II receptor is a serine/threonine receptor kinase, which catalyses the phosphorylation of the Type I receptor. Each class of ligand binds to a specific type II receptor. In mammals there are seven known type I receptors and five type II receptors.

There are three activins: Activin A, Activin B and Activin AB. Activins are involved in embryogenesis and osteogenesis. They also regulate many hormones including pituitary, gonadal and hypothalamic hormones as well as insulin. They are also nerve cell survival factors.

The BMPs bind to the Bone morphogenetic protein receptor type-2 (BMPR2). They are involved in a multitude of cellular functions including osteogenesis, cell differentiation, anterior/posterior axis specification, growth, and homeostasis.

The TGF beta family include: TGFβ1, TGFβ2, TGFβ3. Like the BMPS, TGF betas are involved in embryogenesis and cell differentiation, but they are also involved in apoptosis, as well as other functions. They bind to TGF-beta receptor type-2 (TGFBR2).

Nodal binds to activin A receptor, type IIB ACVR2B. It can then either form a receptor complex with activin A receptor, type IB (ACVR1B) or with activin A receptor, type IC (ACVR1C).

The TGF beta signaling pathway (Table 1) is involved in a wide range of cellular process and subsequently is very heavily regulated. There are a variety of mechanisms that the pathway is modulated both positively and negatively: There are agonists for ligands and R-SMADs; there are decoy receptors; and R-SMADs and receptors are ubiquitinated.

TABLE 1

TGF beta signaling pathway

| TGF Beta superfamily ligand | Type II Receptor | Type I receptor | R-SMADs | coSMAD | Ligand inhibitors |
|---|---|---|---|---|---|
| Activin A | ACVR2A | ACVR1B (ALK4) | SMAD2, SMAD3 | SMAD4 | Follistatin |
| GDF1 | ACVR2A | ACVR1B (ALK4) | SMAD2, SMAD3 | SMAD4 | |
| GDF11 | ACVR2B | ACVR1B (ALK4), TGFβRI (ALK5) | SMAD2, SMAD3 | SMAD4 | |
| Bone morphogenetic proteins | BMPR2 | BMPR1A (ALK3), BMPR1B (ALK6) | SMAD1, SMAD5, SMAD8 | SMAD4 | Noggin, Chordin, DAN |
| Nodal | ACVR2B | ACVR1B (ALK4), ACVR1C (ALK7) | SMAD2, SMAD3 | SMAD4 | Lefty |
| TGFβs | TGFβRII | TGFβRI (ALK5) | SMAD2, SMAD3 | SMAD4 | LTBP1, THBS1, Decorin |

In certain embodiments the compositions and methods of the present invention comprise adjustment of activity of transforming growth factor beta (TGF-β) or a TGF-β family member or variants or functional fragments thereof to determine an appropriate or optimal differentiation condition.

As used herein, the term "member of the TGF-β family" or the like refers to growth factors that are generally characterized by one of skill in the art as belonging to the TGF-β family, either due to homology with known members of the TGF-β family, or due to similarity in function with known members of the TGF-β family. In particular embodiments of the invention, if the member of the TGF-43 family is present, the TGF-β family member of variant or functional fragment thereof activates SMAD 2 or 3. In certain embodiments, the member of the TGF-β family is selected from the group consisting of Nodal, Activin A, Activin B, TGF-β, bone morphogenic protein-2 (BMP2) and bone morphogenic protein-4 (BMP4). In one embodiment, the member of the TGF-β family is Activin A.

It is contemplated that if Nodal is present, it may be varied from a concentration of approximately 0.1 ng/mL to approximately 2000 ng/ml, more preferably approximately 1 ng/mL to approximately 1000 ng/ml, more preferably approximately 10 ng/mL to approximately 750 ng/ml, or more preferably approximately 25 ng/mL to approximately 500 ng/ml. It is contemplated that if used, Activin A may be varied at a concentration of approximately 0.01 ng/mL to approximately 1000 ng/ml, more preferably approximately 0.1 ng/mL to approximately 100 ng/ml, more preferably approximately 0.1 ng/mL to approximately 25 ng/ml, or most preferably at a concentration of approximately 6 to 20 ng/ml. It is contemplated that if present, TGF-β may be varied present at a concentration of approximately 0.01 ng/mL to approximately 100 ng/ml, more preferably approximately 0.1 ng/mL to approximately 50 ng/ml, or more preferably approximately 0.1 ng/mL to approximately 20 ng/ml.

In certain embodiments, the compositions and methods comprise an inhibitor or an inactivator of Activin/Nodal signaling. As used herein, an "inhibitor or inactivator of Activin/Nodal signaling" refers to an agent that antagonizes the activity of one or more Activin/Nodal proteins or any of their upstream or downstream signaling components through any of its possible signaling pathways. Non-limiting examples include SB-431542.

In certain embodiments, the compositions and methods comprise an inhibitor or an inactivator of BMP signaling. As used herein, an "inhibitor or inactivator of BMP signaling" refers to an agent that antagonizes the activity of one or more BMP proteins or any of their upstream or downstream signaling components through any of its possible signaling pathways. The compound(s) used to inactivate BMP signaling can be any compound known in the art, or later discovered. Non-limiting examples of inhibitors of BMP signaling include dorsomorphin, dominant-negative, truncated BMP receptor, soluble BMP receptors, BMP receptor-Fc chimeras, noggin, follistatin, chordin, gremlin, cerberus/DAN family proteins, ventropin, high dose activin, and amnionless.

VI. Non-Static Culture

In certain aspects, non-static culture could be used for culturing and differentiation of pluripotent stem cells. Suspension culture can be used to produce large scale of EBs and differentiated cells subsequently; however, static culture has little control over the size and shape of EBs formed, which directly influence yield and quality of cells differentiated therefrom. The non-static culture can be any culture with cells kept at a controlled moving speed, by using, for example, shaking, rotating, or stirring platforms or culture vessels, particularly large-volume rotating bioreactors. The agitation may improve circulation of nutrients and cell waste products and also be used to control cell aggregation by providing a more uniform environment. For example, rotary speed may be set to at least or at most about 25, 30, 35, 40, 45, 50, 75, 100 rpm, or any range derivable therein. The incubation period in the non-static culture for pluripotent stem cells, cell aggregates, differentiated stem cells, or progeny cells derived therefrom, may be at least or about 4 hours, 8 hours, 16 hours, or 1, 2, 3, 4, 5, 6 days, or 1, 2, 3, 4, 5, 6, 7 weeks, or any range derivable therein.

VII. Cardiomyocyte Lineage Differentiation and Characterization

Cardiomyocyte lineage cells can be obtained from undifferentiated stem cells by culturing or differentiating in a special growth environment that enriches for cells with the desired phenotype (either by outgrowth of the desired cells, or by inhibition or killing of other cell types). Cardiomyocyte may be differentiated from a selected pluripotent stem cell clone in a differentiation medium prepared from a selected batch of culture medium under a previously determined optimal condition suitable for the specific clone-medium combination. The optimal condition may be determined by screening of the highest differentiation efficiency among a variety of test conditions, such as timing and/or level of addition of external differentiation factors.

In certain aspects, the iPS cells may be differentiated into cardiac cells in cell suspension incorporating the disclosed methods. Differentiation can be initiated by forming embryoid bodies or aggregates as described above: for example, by overgrowth of a pluripotent stem cell culture, or by culturing pluripotent stem cells in suspension in culture vessels having a substrate with low adhesion properties which allows EB formation. Pluripotent stem cells could be harvested by brief collagenase digestion, dissociated into clusters, and plated in non-adherent cell culture plates (WO 01/51616; U.S. Pat. No. 6,602,711, incorporated by reference). Optionally, the EBs can be produced encapsulated in alginate or other suitable nutrient-permeable matrix, which may help improve the uniformity of EB diameter and consistency of the cells produced (WO 03/004626, Zandstra et al., incorporated by reference).

Whether or not the process involves EB formation, using a medium that contains serum or serum equivalent promotes foci of contracting cells of the cardiomyocyte lineage: for example, about 20% fetal bovine serum, or a serum supplement such as B27 or N2 in a suitable growth medium such as RPMI. More exemplary methods of cardiac differentiation may include embryoid body (EB) methods (Zhang, et al., 2009, which is incorporated by reference), OP9 stroma cell methods (Narazaki, et al., 2008, which is incorporated by reference), or growth factor/chemical methods (see U.S. Patent Publication Nos. 20080038820, 20080226558, 20080254003 and 20090047739, all incorporated herein by reference in their entirety).

To promote the cardiomyocyte phenotype, the cells can be cultured with differentiation factors and factor combinations that enhance proliferation or survival of cardiomyocyte type cells, or inhibit the growth of other cell types. The effect may be due to a direct effect on the cell itself, or due to an effect on another cell type, which in turn enhances cardiomyocyte formation. For example, factors that induce the formation of hypoblast or epiblast equivalent cells, or cause these cells to produce their own cardiac promoting elements, all come within the rubric of cardiomyocyte differentiation factors.

For example, medium for cardiac differentiation may include, but is not limited to, precardiac explants, precardiac mesoderm conditioned medium, and mesoderm secreted growth factors such as HGF.

Differentiation factors thought to induce differentiation of pluripotent stem cells into cells of the mesoderm layer, or facilitate further differentiation into cardiomyocyte lineage cells include the following:

Transforming Growth Factor beta-related ligands (exemplified by TGF-β1, TGF-β2, TGF-β3 and other members of the TGF-β superfamily illustrated below). Ligands bind a TGF-β receptor activate Type I and Type II serine kinases and cause phosphorylation of the Smad effector.

Morphogens like Activin A and Activin B (members of the TGF-β superfamily).

Insulin-like growth factors (such as IGF I and IGF II).

Bone morphogenic proteins (members of the TGF-β superfamily, exemplified by BMP-2 and BMP-4).

Fibroblast growth factors (exemplified by bFGF, FGF-4, and FGF-8), other ligands that activate cytosolic kinase raf-1 and mitogen-activated proteins kinase (MAPK), and other mitogens such as epidermal growth factor (EGF).

Nucleotide analogs that affect DNA methylation and altering expression of cardiomyocyte-related genes (e.g., 5-azadeoxy-cytidine).

The pituitary hormone oxytocin, or nitric oxide (NO).

Specific antibodies or synthetic compounds with agonist activity for the same receptors.

Exemplary effective combinations of differentiation factors include use of a morphogen like Activin A and a plurality of growth factors, such as those included in the TGF-β and IGF families during the early commitment stage, optionally supplemented with additional cardiotropins such as one or more fibroblast growth factors, bone morphogenic proteins, and platelet-derived growth factors.

The combination or concentration of any differentiation factors described above may be varied to determine the optimal condition for a selected stem cell clone in a selected batch of culture medium. One or more differentiation factors may be varied at a concentration of two or more levels selected from a range including at least or about 5, 10, 15, 20, 25, 30, 35, 40, 45, 50, 55, 60, 65, 70, 75, 80, 85, 90, 95, 100, 150, 180, 200, 250 ng/ml or any range derivable therein.

During the elaboration of this invention, it was found that omitting factors such as insulin-like growth factor II (IGF II) and related molecules from the final stages of in vitro differentiation actually increase the levels of cardiac gene expression. In unrelated studies, IGF II has been found to decrease the levels of GSK3β in fibroblasts (Scalia et al., 2001). IGF II may therefore potentiate the effects of Wnt proteins present in the culture medium or secreted by the cells. Wnt proteins normally stabilize and cause nuclear translocation of a cytoplasmic molecule, β-catenin, which comprises a portion of the transcription factor TCF. This changes transcriptional activity of multiple genes. In the absence of Wnt, β-catenin is phosphorylated by the kinase GSK3β, which both destabilizes β-catenin and keeps it in the cytoplasm.

Since Wnt activators like IGF II apparently limit cardiomyocyte differentiation, certain aspects of this invention may include culturing with Wnt antagonists to increase the extent or proportion of cardiomyocyte differentiation of pluripotent stem cells. Wnt signaling can be inhibited by injection of synthetic mRNA encoding either DKK-1 or Crescent (secreted proteins that bind and inactivate Wnts) (Schneider et al., 2001), or by infection with a retrovirus encoding DKK-1 (Marvin et al., 2001). Alternatively, the Wnt pathway can be inhibited by increasing the activity of the kinase GSK3β, for example, by culturing the cells with factors such as IL-6 or glucocorticoids.

In a certain embodiment, FGF or a combination of FGF and HGF are used to culture pluripotent stem cells, cell aggregates, or differentiated stem cells, which may promote cardiac induction of stem cells. For example, FGF may be added at a concentration of at least or about 5, 10, 15, 20, 25, 30, 35, 40, 45, 50, 55, 60, 65, 70, 75, 80, 85, 90, 95, 100, 150, 180, 200, 250 ng/ml or any range derivable therein. Optionally hepatic growth factor (HGF) may also be included, for example at a concentration of at least or about 5, 10, 15, 20, 25, 30, 35, 40, 45, 50, 55, 60, 65, 70, 75, 80, 85, 90, 95, 100, 150, 180, 200, 250 ng/ml or any range derivable therein.

The cells obtained according to the techniques of this invention can be characterized according to a number of phenotypic criteria. Cardiomyocytes and precursor cells derived from pluripotent stem cell lines often have morphological characteristics of cardiomyocytes from other sources. They can be spindle, round, triangular or multi-angular shaped, and they may show striations characteristic of sarcomeric structures detectable by immunostaining. They may form flattened sheets of cells, or aggregates that stay attached to the substrate or float in suspension, showing typical sarcomeres and atrial granules when examined by electron microscopy.

Pluripotent stem cell-derived cardiomyocytes and their precursors typically have at least one of the following cardiomyocyte specific markers:

Cardiac troponin I (cTnI), a subunit of troponin complex that provides a calcium-sensitive molecular switch for the regulation of striated muscle contraction.

Cardiac troponin T (cTnT).

Nkx2.5, a cardiac transcription factor expressed in cardiac mesoderm during early mouse embryonic development, which persists in the developing heart.

The cells may also express at least one (and often at least 3, 5, or more) of the following markers:

Atrial natriuretic factor (ANF), a hormone expressed in developing heart and fetal cardiomyocytes but down-regulated in adults. It is considered a good marker for cardiomyocytes because it is expressed in a highly specific manner in cardiac cells but not skeletal myocytes.

Myosin heavy chain (MHC), particularly the β chain which is cardiac specific

Titin, tropomyosin, .alpha.-sarcomeric actinin, and desmin

GATA-4, a transcription factor that is highly expressed in cardiac mesoderm and persists in the developing heart. It regulates many cardiac genes and plays a role in cardiogenesis MEF-2A, MEF-2B, MEF-2C, MEF-2D; transcription factors that are expressed in cardiac mesoderm and persist in developing heart N-cadherin, which mediates adhesion among cardiac cells Connexin 43, which forms the gap junction between cardiomyocytes.

β1-adrenoceptor (β2-AR)

Creatine kinase MB (CK-MB) and myoglobin, which are elevated in serum following myocardial infarction α-cardiac actin, early growth response-I, and cyclin D2.

Tissue-specific markers can be detected using any suitable immunological technique—such as flow immunocytometry or affinity adsorption for cell-surface markers, immunocytochemistry (for example, of fixed cells or tissue sections) for intracellular or cell-surface markers, Western blot analysis of cellular extracts, and enzyme-linked immunoassay, for cellular extracts or products secreted into the medium. Antibodies that distinguish cardiac markers like cTnI and cTnT from other isoforms are available commercially from suppliers like Sigma and Spectral Diagnostics. Expression of an antigen by a cell is said to be antibody-detectable if a significantly detectable amount of antibody will bind to the antigen in a standard immunocytochemistry or flow cytometry assay, optionally after fixation of the cells, and optionally using a labeled secondary antibody.

The expression of tissue-specific gene products can also be detected at the mRNA level by Northern blot analysis, dot-blot hybridization analysis, or by reverse transcriptase initiated polymerase chain reaction (RT-PCR) using sequence-specific primers in standard amplification methods using publicly available sequence data (GenBank). Expression of tissue-specific markers as detected at the protein or mRNA level is considered positive if the level is at least or about 2-, 3-, 4-, 5-, 6-, 7-, 8-, or 9-fold, and more particularly more than 10-, 20-, 30, 40-, or 50-fold above that of a control cell, such as an undifferentiated pluripotent stem cell or other unrelated cell type.

Once markers have been identified on the surface of cells of the desired phenotype, they can be used for immunoselection to further enrich the population by techniques such as immunopanning or antibody-mediated fluorescence-activated cell sorting.

Under appropriate circumstances, pluripotent stem cell-derived cardiomyocytes often show spontaneous periodic contractile activity. This means that when they are cultured in a suitable tissue culture environment with an appropriate $Ca^{2+}$ concentration and electrolyte balance, the cells can be observed to contract across one axis of the cell, and then release from contraction, without having to add any additional components to the culture medium. The contractions are periodic, which means that they repeat on a regular or irregular basis, at a frequency between about 6 and 200 contractions per minute, and often between about 20 and about 90 contractions per minute in normal buffer. Individual cells may show spontaneous periodic contractile activity on their own, or they may show spontaneous periodic contractile activity in concert with neighboring cells in a tissue, cell aggregate, or cultured cell mass.

The contractile activity of the cells can be characterized according to the influence of culture conditions on the nature and frequency of contractions. Compounds that reduce available $Ca^{2+}$ concentration or otherwise interfere with trans-membrane transport of $Ca^{2+}$ often affect contractile activity. For example, the L-type calcium channel blocker diltiazem inhibits contractile activity in a dose-dependent manner. On the other hand, adrenoceptor agonists like isoprenaline and phenylephrine have a positive chronotropic effect. Further characterization of functional properties of the cell can involve characterizing channels for $Na^+$, $K^+$, and $Ca^{2+}$. Electrophysiology can be studied by patch clamp analysis for cardiomyocyte like action potentials. See Igelmund et al., 1999; Wobus et al., 1995; and Doevendans et al., 2000.

Functional attributes provide a manner of characterizing cells and their precursors in vitro, but may not be necessary for some of the uses referred to in this disclosure. For example, a mixed cell population enriched for cells bearing some of the markers listed above, but not all of the functional or electrophysiology properties, can be of considerable therapeutic benefit if they are capable of grafting to impaired cardiac tissue, and acquiring in vivo the functional properties needed to supplement cardiac function.

Where derived from an established line of pluripotent stem cells, the cell populations and isolated cells of this invention can be characterized as having the same genome as the line from which they are derived. This means that the chromosomal DNA will be over 90% identical between the pluripotent stem cells and the cardiac cells, which can be inferred if the cardiac cells are obtained from the undifferentiated line through the course of normal mitotic division. The characteristic that cardiomyocyte lineage cells are derived from the parent cell population is important in several respects. In particular, the undifferentiated cell population can be used for producing additional cells with a shared genome—either a further batch of cardiac cells, or another cell type that may be useful in therapy—such as a population that can pre-tolerize the patient to the histocompatibility type of the cardiac allograft (US 2002/0086005; WO 03/050251).

VIII. Neuron Lineage Characterization

To determine appropriate or optimal condition for differentiation of pluripotent stem cells into a neural lineage for the selected stem cell clone and the batch culture medium, neural lineage characteristics may be assessed to determine differentiation efficiency toward the desired lineage.

In particular embodiments, the neural lineage cells may be characterized by expressing one or more of the detectable markers for tyrosine hydroxylase (TH), vesicular monamine transporter (VMAT) dopamine transporter (DAT), and aromatic amino acid decarboxylase (AADC, also known as dopa decarboxylase). For example, one or more of the differentiated pluripotent stem cells express detectable markers for TH, VMAT, DAT, and AADC. In other embodiments, the neural cell is capable of expressing one or more of the detectable markers for nestin, Sox1, and Map2. For example, the cultured cell expresses detectable markers for nestin, Sox1, and Map2. Such a culture of cells can be produced by the methods described herein or by other methods later developed.

Neural cells can be characterized according to a number of phenotypic criteria. The criteria include but are not limited to microscopic observation of morphological features, detection or quantitation of expressed cell markers, enzymatic activity, neurotransmitters and their receptors, and electrophysiological function.

Certain cells embodied in this invention have morphological features characteristic of neuronal cells or dopaminergic neural cells. These features are recognized by those of skill in the art. For example, neurons include small cell bodies, and multiple processes reminiscent of axons and dendrites.

Neural cells can also be characterized according to whether they express phenotypic markers characteristic of particular kinds of neural cells. Markers of interest include but are not limited to: a) β3-tubulin, microtubule-associated protein 2 (MAP-2), or neurofilament, characteristic of neurons; b) glial fibrillary acidic protein (GFAP), present in astrocytes; c) 2', 3'-cyclic nucleotide 3'-phosphodiesterase (CNPase) galactocerebroside (GalC) or myelin basic protein (MBP), characteristic of oligodendrocytes; d) Oct-4, characteristic of undifferentiated ES cells; e) Pax 6 and nestin, characteristic of neural precursors and other cells; f) Sox 1, characteristic of developing central nervous system; g) tyrosine hydroxylase (TH), present in dopaminergic neurons; h) glutamic acid decarboxylase, isoform 67 (GAD67), present in neurons containing gamma-aminobutyric acid; i) vimentin, characteristic of intermediate neuronal differentiation; j) doublecortin (Dcx); and k) synapsin.

Also characteristic of neural cells, particularly terminally differentiated cells like dopaminergic neurons, are receptors and enzymes involved in the biosynthesis, release, and reuptake of neurotransmitters, and ion channels involved in the depolarization and repolarization events that relate to synaptic transmission. Evidence of synapse formation can be obtained by staining for synaptophysin. Evidence for receptivity to certain neurotransmitters can be obtained by detecting receptors for gamma amino butyric acid (GABA), glutamate, dopamine, 3,4-dihydroxyphenylalanine (DOPA), noradrenaline, acetylcholine, and serotonin.

IX. Hepatocytes Lineage Characterization

To determine appropriate or optimal condition for differentiation of pluripotent stem cells into a hepatocyte lineage for the selected stem cell clone and the batch culture medium, definitive endoderm or hepatocyte lineage characteristics may be assessed to determine differentiation efficiency toward the desired lineage.

Cells can be characterized according to a number of phenotypic criteria. The criteria include but are not limited to the detection or quantification of expressed cell markers, enzymatic activity, and the characterization of morphological features and intercellular signaling. In other aspects, cells to be programmed may comprise reporter gene expression cassette comprising tissue- or cell-specific transcriptional regulatory element, like hepatocyte-specific promoters for hepatocyte identification.

Endoderm, (sometimes called Entoderm) is one of the germ layers formed during animal embryogenesis. Cells migrating inward along the archenteron form the inner layer of the gastrula, which develops into the endoderm. The endoderm consists at first of flattened cells, which subsequently become columnar. It forms the epithelial lining of multiple systems. Hepatic endoderm markers may include CD29 (Integrin (31), CD44H (Pgp-1, H-CAM), CD49f (Integrin α6), CD90 (Thy-1), HNF-1α, HNF-1β (TCF-2), or Tat-SF1. Definitive endoderm markers may include, but not be limited to, Sox 17, FoxA2 and low or negative Sox7.

Hepatocytes embodied in certain aspects of this invention have morphological features characteristic of hepatocytes in the nature. The features are readily appreciated by those skilled in evaluating such things, and include any or all of the following: a polygonal cell shape, a binucleate phenotype, the presence of rough endoplasmic reticulum for synthesis of secreted protein, the presence of Golgi-endoplasmic reticulum lysosome complex for intracellular protein sorting, the presence of peroxisomes and glycogen granules, relatively abundant mitochondria, and the ability to form tight intercellular junctions resulting in creation of bile canalicular spaces. A number of these features present in a single cell are consistent with the cell being a member of the hepatocyte lineage. Unbiased determination of whether cells have morphologic features characteristic of hepatocytes can be made by coding micrographs of programming progeny cells, adult or fetal hepatocytes, and one or more negative control cells, such as a fibroblast, or RPE (Retinal pigment epithelial) cells—then evaluating the micrographs in a blinded fashion, and breaking the code to determine if the hepatocytes from differentiation are accurately identified.

Cells of this invention can also be characterized according to whether they express phenotypic markers characteristic of cells of the hepatocyte lineage. Non-limiting examples of cell markers useful in distinguishing hepatocytes include albumin, asialoglycoprotein receptor, α1-antitrypsin, α-fetoprotein, apoE, arginase I, apoAI, apoAII, apoB, apoCIII, apoCII, aldolase B, alcohol dehydrogenase 1, catalase, CYP3A4, glucokinase, glucose-6-phosphatase, insulin growth factors 1 and 2, IGF-1 receptor, insulin receptor, leptin, liver-specific organic anion transporter (LST-1), L-type fatty acid binding protein, phenylalanine hydroxylase, transferrin, retinol binding protein, and erythropoietin (EPO). Mature hepatocyte markers include, but are limited to, albumin, α1-antitrypsin, asialoglycoprotein receptor, cytokeratin 8 (CK8), cytokeratin 18 (CK18), CYP3A4, fumaryl acetoacetate hydrolase (FAH), glucose-6-phosphates, tyrosine aminotransferase, phosphoenolpyruvate carboxykinase, and tryptophan 2,3-dioxygenase.

Assessment of the level of expression of such markers can be determined in comparison with other cells. Positive controls for the markers of mature hepatocytes include adult hepatocytes of the species of interest, and established hepatocyte cell lines. The reader is cautioned that permanent cell lines or long-term liver cell cultures may be metabolically altered, and fail to express certain characteristics of primary hepatocytes. Negative controls include cells of a separate lineage, such as an adult fibroblast cell line, or retinal pigment epithelial (RPE) cells. Undifferentiated stem cells are positive for some of the markers listed above, but negative for markers of mature hepatocytes, as illustrated in the examples below.

Cells can also be characterized according to whether they display enzymatic activity that is characteristic of cells of the hepatocyte lineage. For example, assays for glucose-6-phosphatase activity are described by Bublitz (1991); Yasmineh et al. (1992); and Ockerman (1968). Assays for alkaline phosphatase (ALP) and 5-nucleotidase (5'-Nase) in liver cells are described by Shiojiri (1981). A number of laboratories that serve the research and health care sectors provide assays for liver enzymes as a commercial service.

In other embodiments, cells of the invention are assayed for activity indicative of xenobiotic detoxification. Cytochrome p450 is a key catalytic component of the mono-oxygenase system. It constitutes a family of hemoproteins responsible for the oxidative metabolism of xenobiotics (administered drugs), and many endogenous compounds. Different cytochromes present characteristic and overlapping substrate specificity. Most of the biotransforming ability is attributable by the cytochromes designated 1A2, 2A6, 2B6, 3A4, 2C 9-11, 2D6, and 2E1 (Gomes-Lechon et al., 1997).

A number of assays are known in the art for measuring xenobiotic detoxification by cytochrome p450 enzyme activity. Detoxification by CYP3 A4 is demonstrated using the P450-Glo™ CYP3A4 DMSO-tolerance assay (Luciferin-PPXE) and the P450-Glo™ CYP3A4 cell-based/biochemical assay (Luciferin-PFBE) (Promega Inc, #V8911 and #V8901). Detoxification by CYP1A1 and or CYP1B1 is demonstrated using the P450-Glo™ assay (Luciferin-CEE) (Promega Inc., #V8762). Detoxification by CYP1A2 and or CYP4A is demonstrated using the P450-Glo™ assay (Luciferin-ME) (Promega Inc., #V8772) Detoxification by CYP2C9 is demonstrated using the P450-Glo™ CYP2C9 assay (Luciferin-H) (Promega Inc., #V8791).

In another aspect, the biological function of a hepatocyte cell provided by differentiation is evaluated, for example, by analysing glycogen storage. Glycogen storage is characterized by assaying Periodic Acid Schiff (PAS) functional staining for glycogen granules. The hepatocyte-like cells are first oxidized by periodic acid. The oxidative process results in the formation of aldehyde groupings through carbon-to-carbon bond cleavage. Free hydroxyl groups should be present for oxidation to take place. Oxidation is completed when it reaches the aldehyde stage. The aldehyde groups are detected by the Schiff reagent. A colorless, unstable dialdehyde compound is formed and then transformed to the colored final product by restoration of the quinoid chromophoric grouping (Thompson, 1966; Sheehan and Hrapchak, 1987). PAS staining can be performed according the protocol described at http://www.jhu.edu/~iic/PDF jrotocols/LM/Glycogen Staining.pdf and http://library.med.utah.edu/WebPath/HISTHTML/MANUALS/PAS.PDF with some modifications for an in vitro culture of hepatocyte-like cells. One of ordinary skill in the art should be able to make the appropriate modifications.

In another aspect, a hepatocyte cell provided by differentiation in certain aspects the invention is characterized for urea production. Urea production can be assayed colorimetrically using kits from Sigma Diagnostic (Miyoshi et al, 1998) based on the biochemical reaction of urease reduction to urea and ammonia and the subsequent reaction with 2-oxoglutarate to form glutamate and NAD.

In another aspect, bile secretion is analysed. Biliary secretion can be determined by fluorescein diacetate time lapse assay. Briefly, monolayer cultures of hepatocyte-like cells are rinsed with phosphate buffered saline (PBS) three times and incubated with serum-free hepatocyte growth media supplemented with doxycycline and fluorescein diacetate (20 μg/ml) (Sigma-Aldrich) at 37° C. for 35 minutes. The cells are washed with PBS three times and fluorescence imaging is carried out. Fluorescein diacetate is a non fluorescent precursor of fluorescein. The image is evaluated to determine that the compound had been taken up and metabolized in the hepatocyte-like cell to fluorescein. In some embodiments, the compound is secreted into intercellular clefts of the monolayer of cells. Alternatively, bile secretion is determined by a method using sodium fluorescein described by Gebhart and Wang (1982).

In yet another aspect, lipid synthesis is analysed. Lipid synthesis in the hepatocyte-like cell can be determined by oil red O staining. Oil Red O (Solvent Red 27, Sudan Red 5B, C.I. 26125, $C_{26}H_{24}N_4O$) is a lysochrome (fat-soluble dye) diazo dye used for staining of neutral triglycerides and lipids on frozen sections and some lipoproteins on paraffin sections. It has the appearance of a red powder with maximum absorption at 518 (359) nm. Oil Red O is one of the dyes used for Sudan staining. Similar dyes include Sudan III, Sudan IV, and Sudan Black B. The staining has to be performed on fresh samples and/or formalin fixed samples. Hepatocyte-like cells are cultured on microscope slides, rinsed in PBS three times, the slides are air dried for 30-60 minutes at room temperature, fixed in ice cold 10% formalin for 5-10 minutes, and then rinse immediately in 3 changes of distilled water. The slide is then placed in absolute propylene glycol for 2-5 minutes to avoid carrying water into Oil Red O and stained in pre-warmed Oil Red O solution for 8 minutes in 600° C. oven. The slide is then placed in 85% propylene glycol solution for 2-5 minutes and rinsed in 2 changes of distilled water. Oil red 0 staining can also be performed according the protocol described at library.med.utah.edu/WebPath/HISTHTML/MANUALS/OILRED.PDF with some modifications for an in vitro culture of hepatocyte-like cell by one of ordinary skill in the art.

In still another aspect, the cells are assayed for glycogen synthesis. Glycogen assays are well known to one of ordinary skill in the art, for example, in Passonneau and Lauderdale (1974). Alternatively, commercial glycogen assays can be used, for example, from BioVision, Inc. catalog #K646-100.

Cells of the hepatocyte lineage can also be evaluated by their ability to store glycogen. A suitable assay uses Periodic Acid Schiff (PAS) stain, which does not react with mono- and disaccharides, but stains long-chain polymers such as glycogen and dextran. PAS reaction provides quantitative estimations of complex carbohydrates as well as soluble and membrane-bound carbohydrate compounds. Kirkeby et al. (1992)

describe a quantitative PAS assay of carbohydrate compounds and detergents. van der Laarse et al. (1992) describe a microdensitometric histochemical assay for glycogen using the PAS reaction. Evidence of glycogen storage is determined if the cells are PAS-positive at a level that is at least 2-fold, and preferably more than 10-fold above that of a control cell, such as a fibroblast The cells can also be characterized by karyotyping according to standard methods.

Assays are also available for enzymes involved in the conjugation, metabolism, or detoxification of small molecule drugs. For example, cells can be characterized by an ability to conjugate bilirubin, bile acids, and small molecule drugs, for excretion through the urinary or biliary tract. Cells are contacted with a suitable substrate, incubated for a suitable period, and then the medium is analyzed (by GCMS or other suitable technique) to determine whether a conjugation product has been formed. Drug metabolizing enzyme activities include de-ethylation, dealkylation, hydroxylation, demethylation, oxidation, glucuroconjugation, sulfoconjugation, glutathione conjugation, and N-acetyl transferase activity (A. Guillouzo, pp 411-431 in In vitro Methods in Pharmaceutical Research, Academic Press, 1997). Assays include peenacetin de-ethylation, procainamide N-acetylation, paracetamol sulfoconjugation, and paracetamol glucuronidation (Chesne et al., 1988).

A further feature of certain cell populations of this invention is that they are susceptible under appropriate circumstances to pathogenic agents that are tropic for primate liver cells. Such agents include hepatitis A, B, C, and delta, Epstein-Barr virus (EBV), cytomegalovirus (CMV), tuberculosis, and malaria. For example, infectivity by hepatitis B can be determined by combining cultured differentiation-derived hepatocytes with a source of infectious hepatitis B particles (such as serum from a human HBV carrier). The liver cells can then be tested for synthesis of viral core antigen (HBcAg) by immunohistochemistry or RT-PCR.

The skilled reader will readily appreciate that an advantage of programming-derived hepatocytes is that they will be essentially free of other cell types that typically contaminate primary hepatocyte cultures isolated from adult or fetal liver tissue. Markers characteristic of sinusoidal endothelial cells include Von Willebrand factor, CD4, CD14, and CD32. Markers characteristic of bile duct epithelial cells include cytokeratin-7, cytokeratin-19, and γ-glutamyl transpeptidase. Markers characteristic of stellate cells include α-smooth muscle actin (α-SMA), vimentin, synaptophysin, glial fibrillary acidic protein (GFAP), neural-cell adhesion molecule (N-CAM), and presence of lipid droplets (detectable by autofluorescence or staining by oil red O). Markers characteristic of Kupffer cells include CD68, certain lectins, and markers for cells of the macrophage lineage (such as HLA Class II, and mediators of phagocytosis). Differentiation-derived hepatocytes can be characterized as essentially free of some or all of these cell types if less than 0.1% (preferably less than 100 or 10 ppm) bear markers or other features of the undesired cell type, as determined by immunostaining and fluorescence-activated quantitation, or other appropriate technique.

Hepatocytes provided by differentiation according to certain aspects of this invention can have a number of the features of the stage of cell they are intended to represent. The more of these features that are present in a particular cell, the more it can be characterized as a cell of the hepatocyte lineage. Cells having at least 2, 3, 5, 7, or 9 of these features are increasingly more preferred. In reference to a particular cell population as may be present in a culture vessel or a preparation for administration, uniformity between cells in the expression of these features is often advantageous. In this circumstance, populations in which at least about 40%, 60%, 80%, 90%, 95%, or 98% of the cells have the desired features are increasingly more preferred.

Other desirable features of hepatocytes provided in certain aspects of this invention are an ability to act as target cells in drug screening assays, and an ability to reconstitute liver function, both in vivo, and as part of an extracorporeal device. These features are described further in sections that follow.

X. Genetic Alteration of Differentiated Cells

The cells of this invention can be made to contain one or more genetic alterations by genetic engineering of the cells either before or after differentiation (US 2002/0168766). A cell is said to be "genetically altered" or "transgenic" when a polynucleotide has been transferred into the cell by any suitable means of artificial manipulation, or where the cell is a progeny of the originally altered cell that has inherited the polynucleotide. For example, the cells can be processed to increase their replication potential by genetically altering the cells to express telomerase reverse transcriptase, either before or after they progress to restricted developmental lineage cells or terminally differentiated cells (US 2003/0022367).

The cells of this invention can also be genetically altered in order to enhance their ability to be involved in tissue regeneration, or to deliver a therapeutic gene to a site of administration. A vector is designed using the known encoding sequence for the desired gene, operatively linked to a promoter that is either pan-specific or specifically active in the differentiated cell type. Of particular interest are cells that are genetically altered to express one or more growth factors of various types such as FGF, cardiotropic factors such as atrial natriuretic factor, cripto, and cardiac transcription regulation factors, such as GATA-4, Nkx2.5, and MEF2-C. Production of these factors at the site of administration may facilitate adoption of the functional phenotype, enhance the beneficial effect of the administered cell, or increase proliferation or activity of host cells neighboring the treatment site.

In certain embodiments of the invention, cells containing a nucleic acid construct of the present invention may be identified in vitro or in vivo by including a marker in the expression vector, such as a selectable or screenable marker. Such markers would confer an identifiable change to the cell permitting easy identification of cells containing the expression vector, or help enrich or identify differentiated cardiac cells by using a tissue-specific promoter. For example, in the aspects of cardiomyocyte differentiation, cardiac-specific promoters may be used, such as promoters of cardiac troponin I (cTnI), cardiac troponin T (cTnT), sarcomeric myosin heavy chain (MHC), GATA-4, Nkx2.5, N-cadherin, β1-adrenoceptor, ANF, the MEF-2 family of transcription factors, creatine kinase MB (CK-MB), myoglobin, or atrial natriuretic factor (ANF). In aspects of neuron differentiation, neuron-specific promoters may be used, including but not limited to, TuJ-1, Map-2, Dcx or Synapsin. In aspects of hepatocyte differentiation, definitive endoderm- and/or hepatocyte-specific promoters may be used, including but not limited to, ATT, Cyp3a4, ASGPR, FoxA2, HNF4a or AFP.

Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to blasticidin, neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

XI. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Optimizing Cardiomyocyte Differentiation from Different Lines of Pluripotent Stem Cells and after Culture in Different Stem Cell Maintenance Media This Example describes a procedure to maximize the differentiation potential of multiple PSC lines or clones, grown in variable primary culture conditions, to the cardiomyocyte lineage by manipulating the salient signaling pathways, including BMP and Activin/Nodal. This procedure includes: 1) screening the cardiogenic potential of each cell line in a number of conditions, followed by 2) customizing the differentiation protocol for an individual PSC line.

The Manufacturing Procedure as described in U.S. Provisional Application 61/252,919 is followed and modified as detailed below.

At any point during aggregate formation but preferably at day 3 of differentiation, to the typical differentiation culture media (outlined in the Manufacturing Procedure), various combinations of growth factor agonists and antagonists were added. Including: a) No additional growth factors; b) Variable concentrations of BMP4 alone. For example, 1 ng/ml, 5 ng/ml, 10 ng/ml, 20 ng/ml; c) Variable concentrations of Activin alone. For example, 1 ng/ml, 3 ng/ml, 6 ng/ml, 12 ng/ml; d) Variable concentrations of Dorsomorphin; e) Variable concentrations of SB-431542; f) Variable combinations of BMP4 and Activin.

Media were changed daily using the various conditions outlined in previous paragraph, until day 7 of differentiation. After day 7 of differentiation the standard Manufacturing Procedure as described in U.S. Provisional Application 61/252,919 was followed.

At days 6, 7 and 8 of differentation, a small sample was harvested from each condition to monitor for expression of markers consistent with cardiac mesoderm by flow cytometry (Table 2). This information was used to predict optimal culture conditions to differentiate cells into the cardiac lineages. Typically, a 30% KDR+/PDGFR-a+ population is consistent with the successful induction of cardiac mesoderm.

At the endpoint of the assay, typically day 14 of differentiation, the cultures were harvested and analyzed for % of cardiomyocytes based on expression of proteins consistent with cardiomyocyte development (Table 2). In addition, a total cell count was determined.

For example, FIGS. 1A-1D details the results of a growth factor/inhibitor screen utilizing varying concentrations of BMP (1 ng/mL, 10 ng/mL), dorsomorphin (2 uM, 0.2 uM), Activin A (1 ng/mL, 10 ng/mL), SB-431542 (10 uM, 0.1 uM) and a combination of Activin A (6 ng/mL) and BMP4 (10 ng/mL) (variable concentrations of compounds were added at days 3, 4, 5, 6, and 7 of differentiation). Analysis of the cells at day 14 post aggregate formation (FIGS. 1C and 1D) shows a higher concentration of Troponin T (CTNT) positive cells in the treatment comprising a combination of Activin A and BMP4. The presence of CTNT was determined by flow cytometry using an anti-CTNT Antibody. As such, the optimized culture conditions for the stem cell clone iPS 6.1 MRB for differentiation into cardiomyocytes is a combination of Activin A (6 ng/mL) and BMP4 (10 ng/mL).

Based on marker analysis (for example, flow cytometry) from days 6, 7, 8, 9, 10 and/or at earlier or later time points in differentiation and optionally the total yield of cardiomyocytes, the cultures that had the highest yield and/or purity (or another measure of optimal cell culture growth and/or differentiation for the desired differentiated cell type, such as function of a cell-specific enzyme or receptor or electrophysiological function specific for the desired cell type) were identified and, therefore, the corresponding culture conditions are known that resulted in optimal differentiation of the pluripotent stem cell clone utilized. These culture conditions can then be routinely utilized during the Manufacturing Procedure, thereby coupling the pluripotent stem cells from the same cell line or clone with the same culture medium composition, or further manipulations can be investigated to increase the yield.

TABLE 2

Non-limiting Examples of Growth Factors and Markers associated with developmental stages of Cardiac Mesoderm and Cardiomyocytes

| Examples of Growth Factors that induce Cardiac Mesoderm | Examples of Cardiac Mesoderm Markers | Examples of Growth Factors specifying cardiomyocytes | Examples of Cardiomyocyte Markers |
|---|---|---|---|
| Wnt | KDR | BMP2 | NKX2.5 |
| ActivinA/Nodal | PDGFR-a | BMP4 | TBX5 |
| BMP2 | CXCR4 | BMP10 | GATA4 |
| BMP4 | CKITneg | ActivinA/Nodal | Baf60c |
| BMP10 | N-Cadherin | bFGF | alpha-MHC |
| bFGF | MESP1 | EGF | CTNT |
| IGF | | IGF | MLC2A |
| | | (Wnt inhibitors) | MLC2V |
| | | | MLC1V |
| | | | Sarcomeric alpha-actinin |
| | | | NPPA |

Abbreviations and definition
PSC = Pluripotent Stem Cells—Embryonic and Induced Pluripotent Stem Cells.
BMP4 = Bone Morphogenic Protein - 4; Developmental morphogen
Activin = ActivinA (Activin and Nodal signaling can be used interchangeably in this context). Developmental morphogen
SB-431542 = Small molecule inhibitor of the TGFb/Activin/Nodal signaling pathway
Dor = Dorsomorphin. Small molecule inhibitor of the BMP pathway. Also known as Compound C
KDR = Kinase Insert Domain Receptor, also known as VEGFR-2
PDGFR-a = Platelet Derived Growth Factor Receptor - alpha

Example 2

Neuron Growth Factor Titration Procedure iPS cells are maintained on matrigel in TeSR medium (Stem Cell Technologies) and sodium citrate split one passage prior to aggregate formation and grown in T150 flasks, but can be scaled for starting cells in other culture formats. Alternate pluripotent cell culture media, containing varying concentrations of TGFβ and/or bFGF, can be used to optimize neural differentiation of different iPS cell lines or clones. Pluripotent cell cultures are then maintained in TeSR or similar media or can be "primed" or "conditioned" for differentiation for varying lengths of time prior to aggregate formation. Priming of cultures begins 1, 2, or 3 days prior to aggregate formation and may involve adding small molecule inhibitors of the TGFβ or BMP4 pathways to the pluripotent cell culture media, transitioning the cells to DMEM-F12 supplemented with 1×N2, or both strategies in combination. Small molecule inhibitors of TGFβ/Activin/Nodal signaling (SB 431542) and BMP signaling (dorsomorphin) may be used together or individually, for example 5 uM, 10 uM or 20 uM SB 431542 or 1 uM, 2 uM or 5 uM dorsomorphin or some combination of the two, to prime or condition iPS cells for optimal neuron differentiation.

On Day 0 of neuron differentiation (specifically, aggregate formation), cells are harvested from T150 flasks (up to five flasks at one time) and, after media are aspirated, 12 mL of room temperature TrypLE is added to each flask and the cells are incubated at 37° C. for 7 minutes. Meanwhile, one 50 mL conical tube for each T150 is prepared by adding 12 mL DMEM-F12 with 10% FBS. After a 7 minute incubation, pipet cells to dissociate into single cell solution and transfer cell solution into the prepared 50 mL tubes. Cells are centrifuged at 1200 rpm for 5 minutes and the supernatant is aspirated. Each pellet is resuspended in at least 20 mL Aggregate Formation Medium (100% complete mTeSR1 or similar pluripotent cell culture media; mTeSR1 or similar pluripotent media containing SB 431542 and/or dorsomorphin; or DMEM-F12 with 1×N2 supplement, such media to include 10 μM Blebbistatin). The tubes may be combined and cells are counted (CEDEX HiRES cell counter). Cells are diluted to $1.0\times10^6$ cells per mL for both T25 and spinner flasks with Aggregate Formation Media (see above). Concentrated cell suspensions can be directly added to spinner flasks with the appropriate volume of Aggregate Formation Media. Diluted cell stock is counted (CEDEX HiRES cell counter). Five mL of diluted cell stock is dispensed into T25 ULA flasks and 125 mL or 1 L of diluted cell stock is dispensed into 125 mL or 1 L spinner flasks, respectively. Each flask with diluted cells is placed on a rocker or spinner base inside a 37° C. incubator with 7% $CO_2$. Rockers should be rotating at approximately 15 RPM for T25s and spinner flasks should be placed on a magnetic stir platform operating at 70 RPM (for 125 mL spinners) or 40 RPM (for 1 L spinners).

On Day 1, cells in T25 flasks are fed by angling each flask on edge in cell culture hood and allowing the suspended aggregates to settle to the bottom of the flask or spinner flask for 10 minutes. Spent media are aspirated and cells are fed with 5 mL of Aggregate Transition Medium [50% complete mTeSR1 or similar pluripotent cell culture medium, 49.5% of either (i) DMEM-F12, 0.5×N2 supplement (for aggregates formed without DMEM-F12 with 1×N2 supplement priming) or (ii) DMEM-F12 with 1×N2 (for aggregates formed with DMEM-F12 with 1×N2 supplement priming), all of the foregoing with or without some combination of SB 431542 and/or dorsomorphin at the concentrations previously detailed] for T25s, approximately 100 mL for 125 mL spinner flasks and approximately 900 mL for 1 L spinner flasks. The flasks are returned to the 37° C. incubator with 7% $CO_2$ On Days 2 through 6, flasks are handled the same way except cells are fed with Neural Induction Medium (100% DMEM-F12, 1×N2 supplement, with or without some combination of SB 431542 and/or dorsomorphin at the concentrations listed above). Starting on Day 7, flasks are handled in the same way except cells are fed every other day with Neural Maintenance Medium-Suspension (100% DMEM-F12, 1×N2 supplement). Optimal day of aggregate dissociation and plating of individualized cells to 2D culture vessels can vary depending on the differentiation protocol used. Generally, between Day 14 and 21 post-aggregate formation, aggregates are transferred to a conical tube and pelleted with a 30 second spin at 1200 RPM in a centrifuge. The supernatant is aspirated and 1 mL of warm TrypLE per 5 mL of aggregate culture is added and incubated at 37° C. in a waterbath for 5 to 8 minutes. Assess dissociation of the first tube of cells by gently pipetting. If aggregates break apart easily, quench the TrypLE with an equal volume of DMEM-F12 with 10% FBS. If aggregates do not break apart easily, incubate longer and then reassess dissociation followed by quenching. Aggregates are gently dissociated using a P1000 pipetman or serological pipet. The cells are pelleted at 1200 RPM for 5 minutes in a centrifuge. The cells are resuspended in 2.3 mL (or scaled for spinner flasks) of Neural Plating Medium (100% DMEM-F12, 1×B27 supplement, 1×N2 supplement, 10 uM Blebbistatin). Cells are counted in suspension on CEDEX and the concentration is adjusted to 500,000 cells per mL with Neural Plating Medium. Cells are counted again on CEDEX. To each well of a Matrigel coated 6-well plate (seeded at approximately 1 million cells per well), 2 mL of cell suspension are added, which can be scaled appropriately to seed T150 flasks (30 mL) or double CellStacks (260 mL). The day after plating of dissociated aggregates and two days after that (such as, for example, Days 15 and 17 or Days 22 and 24 depending on protocol), spent media are aspirated and 2D culture vessels are fed Neural Maintenance Medium-Attached (100% DMEM-F12, 1×B27 supplement, 1×N2 supplement) as follows: 2 mL media per well of a 6 well plate, 30 mL per T150 and 260 mL per double CellSTACK. Following four days (two feedings) of Neural Maintenance Medium-Attached, cultures are fed every other day with Neural Maturation Medium (100% DMEM-F12, 1×B27 supplement, 1×N2 supplement, 2.5 uM DAPT) until appropriate maturity is achieved. Neurons may be enriched or selected for during the differentiation procedure by utilizing a pluripotent stem cell clone containing an antibiotic resistance gene (such as, for example, a gene conferring resistance to blasticidin, neomycin, puromycin, or hygromycin) or a screenable marker (such as, for example, a fluorescent protein) under the regulation of a neuron specific promoter (such as, for example, Dcx, TuJ-1, or Map-2). At the end of the differentiation procedure (Day 30 to 45), cells are tested for: 1) purity by flow cytometry with βIII-tubulin/Nestin and/or DCX/Nestin double stains, 2) relative composition of neural subtypes (such as, for example, Dopaminergic, GABAergic or Glutamatergic) by immunocytochemistry, and 3) desired neural function by electrophysiology (such as, for example, single cell patch clamp or multielectrode array).

Example 3

Hepatocyte Growth Factor Titration Procedure iPS cells are maintained on Matrigel in TeSR medium (Stem Cell Technologies) and sodium citrate split. Alternate pluripotent cell culture media, containing varying concentrations of TGFβ and/or bFGF, can be used to optimize hepatocyte differentiation of different iPS cell lines or clones. Pluripotent cell cultures are then maintained in TeSR or similar media or can be "primed" or "conditioned" for differentiation for varying lengths of time prior to aggregate formation. Priming of cultures, if required, begins 1, 2, or 3 days prior to aggregate formation and may involve adding growth factors and/or small molecule inhibitors of TGFβ signalling to the pluripotent cell culture media, transitioning the cells to hepatocyte growth media as described below, or both strategies in combination. As a nonlimiting example, growth factors and small molecule inhibitors of TGFβ signaling can be used in the concentrations detailed below.

On Day 0 of differentiation (specifically, aggregate formation), cells are harvested from T150 flasks and, after media are aspirated, 12 mL of room temperature TrypLE is added and the cells are incubated at 37° C. for 7 minutes. Meanwhile, one 50 mL conical tube for each T150 is prepared by adding 12 mL DMEM/F12 with 10% FBS. After a 7 minute incubation, the flask is tapped to dislodge residual cells, which are pipetted into the prepared 50 mL tubes. Cells are centrifuged at 1200 rpm for 5 minutes and the supernatant is aspirated. The pellet is resuspended in 10 mL Aggregate Formation Medium (100% complete mTeSR, 25 μg/mL gentamicin and 10 M blebbistatin). The tubes are combined into a single conical tube and cells are counted (CEDEX HiRES cell counter). Cells are diluted to $1.0 \times 10^6$ cells per mL and transferred to a spinner flask.

On Day 1 of differentiation, the culture is subdivided into separate T-flasks (number to be determined based on number of TGF-β signaling factor titration samples needed), small aggregates are allowed to settle for thirty minutes, spent media are aspirated, each flask is shaken gently to break up the sheet of cells at the bottom of each flask and Hepatocyte Transition Medium (50% complete mTeSR, 49% RPMI, 1% 50×B27 nutrient supplement, 25 μg/mL gentamicin) is added, which has been supplemented with the following growth factor and inhibitor combinations: no additional growth factors or inhibitors; variable concentrations of Activin A alone, for example 10 ng/mL, 20 ng/mL, 40 ng/mL or 100 ng/mL; variable concentrations of GDF-3 alone, for example 5 ng/mL, 10 ng/mL, 40 ng/mL or 100 ng/mL; variable concentrations of SB-431542, for example 5 μM, 10 μM, 30 M or 60 μM; variable concentrations of BMP4, for example 0.1 ng/mL, 0.5 ng/mL, 1 ng/mL or 5 ng/mL; and variable 2-way combinations of Activin A, GDF-3, SB-431542, and BMP4, for example 20 ng/mL Activin A and 10 ng/mL GDF-3 or 40 ng/mL Activin A and 0.5 ng/mL BMP4. Flasks are placed on a rocker in a 37° C. incubator to provide constant agitation. After 24 hours, the cells are fed Endoderm Induction Medium [98% RPMI, 2% B27 (50× stock), 25 ug/mL Gentamicin], which has been supplemented with the concentrations of TGF-β signaling growth factors/inhibitors per flask consistent with the previous day's treatments and cultured in the same manner. Each condition is either continued in this medium for 1, 2 or 3 days on a daily feeding schedule. At the completion of the Endoderm Induction Medium culturing phase (either 1, 2 or 3 days as previously described), total cell counts are obtained, a 5 mL sample is taken from each flask, and the cells are assessed by flow cytometry for Sox 17, FoxA2 and Sox7, which provides a means of assessing whether the cells exhibit markers consistent with definitive endoderm ($SOX17^+/FOXA2^+/SOX7^-$). Cells are processed as previously described and cultured in Hepatocyte Induction Medium (98% RPMI, 2% B27 (50× stock), 20 ng/mL HGF, 10 ng/mL bFGF, 50 ng/mL BMP4, 25 ug/mL Gentamicin) for 10 days with media changes occurring daily regardless of previous TGF-β signaling growth factor/inhibitor treatment regimen. Cells are then cultured in Hepatocyte Maturation Media (98% RPMI, 2% B27 (50× stock), 20 ng/mL Oncostatin M, 1 μM Dexamethasone, 25 μg/mL Gentamicin) for 10 additional days regardless of previous treatment with media changes occurring every other day. Hepatocytes may be enriched or selected for during the differentiation procedure by initially utilizing a pluripotent stem cell clone in the process that contains an antibiotic resistance gene (such as, for example, a gene conferring resistance to blasticidin, neomycin, puromycin, or hygromycin) or a screenable marker (such as, for example, a fluorescent protein) under the regulation of a hepatocyte specific promoter (such as, for example, Cyp3a4, AAT, or ASGPR). At the end of the differentiation procedure, cells are tested for albumin secretion, ureagenesis, purity by flow cytometry (alpha-1-antitrypsin, albumin, asialogycoprotein receptor 1) and Cyp3a4 activity (P450-GLO kit, Promega), all to assess hepatocyte function.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

References

The following references, to the extent that they provide exemplary procedural or other details supplementary to those set forth herein, are specifically incorporated herein by reference.

U.S. Appln. 61/058,858
U.S. Appln. 61/172,079
U.S. Appln. 61/184,546
U.S. Appln. 61/252,919
U.S. Pat. No. 5,478,838
U.S. Pat. No. 5,843,780
U.S. Pat. No. 6,200,806
U.S. Pat. No. 6,602,711
U.S. Pat. No. 6,833,269
U.S. Pat. No. 7,029,913
U.S. Patent Publn. 2002/0086005
U.S. Patent Publn. 2002/0168766
U.S. Patent Publn. 2002/0076976
U.S. Patent Publn. 2003/0022367
U.S. Patent Publn. 2003/0059913
U.S. Patent Publn. 2003/0062225
U.S. Patent Publn. 2003/0062227
U.S. Patent Publn. 2003/0087919
U.S. Patent Publn. 2003/0125344
U.S. Patent Publn. 2003/0211603
U.S. Patent Publn. 2004/0002507
U.S. Patent Publn. 2004/0002508
U.S. Patent Publn. 2004/0039796
U.S. Patent Publn. 2004/0014755
U.S. Patent Publn. 2005/0192304
U.S. Patent Publn. 2005/0209261

U.S. Patent Publn. 2007/0116680
U.S. Patent Publn. 2007/0238170
U.S. Patent Publn. 2008/0038820
U.S. Patent Publn. 2008/0171385.
U.S. Patent Publn. 2008/0226558
U.S. Patent Publn. 2008/0254003
U.S. Patent Publn. 2009/0047739
Amit et al., *Dev. Bio.*, 227:271-278, 2000.
Andrews et al., In: *Teratocarcinomas and Embryonic Stem Cells*, Robertson (Ed.), IRL Press, 207-246, 1987.
*Animal Cell Culture*, Freshney (Ed.), 1987.
Bublitz, *Mol. Cell. Biochem.*, 108(2):141-4, 1991.
Byrne et al., *Nature*, 450(7169):497-502, 2007.
Chen et al., *Cell*, 133:1106-1117, 2008.
Chesne et al., In: *Liver Cells and Drugs*, Guillouzo (Ed.), John Libbey Eurotext, London, 343-350, 1988
Current Protocols in Molecular Biology and Short Protocols in Molecular Biology, 1987 and 1995.
Doe et al., *J. Pharmacol. Exp. Ther.*, 32:89-98, 2007.
Doevendans et al., *J. Mol. Cell. Cardiol.*, 32:839, 2000.
Embryonic Stem Cell Differentiation in vitro, 1993.
Evans et. al., *Nature*, 292:154, 1981.
Fernandes, et al., *J. Biotechnology*, 132(2):227-236, 2007.
Gebhart and Wang, *J. Cell Sci.*, 56233-244, 1982.
Gene Targeting, A Practical Approach, IRL Press at Oxford University Press, 1993.
Gene Transfer Vectors for Mammalian Cells, 1987.
Gomez-Lechon et al., *Anal. Biochem.*, 236:296, 1996.
Greber et al., *Stem Cells*, 25:455-464, 2007.
Guide to Techniques in Mouse Development, 1993.
Harb et al., *PLoS One*, 20; 3(8):e3001, 2008.
Igelmund et al., *Pflugers Arch.*, 437:669, 1999.
In vitro Methods in Pharmaceutical Research, Guillouzo (Ed.), Academic Press, 411-431, 1997.
Ishizaki, et al., *Mol. Pharmacol.*, 57:976-983, 2000.
Jainchill et al., *J. Virol.*, 4:549, 1969.
Keller et al., *Curr. Opin. Cell Biol.*, 7:862-869, 1995.
Kirkeby et al., *Biochem. Biophys. Meth.*, 24:225, 1992.
Klimanskaya et al., *Lancet.*, 365:P1636-1641, 2005.
Kodama et al., *J. Cell. Physiol.*, 112:89, 1982.
Ludwig et al., *Nat. Biotechnol.*, 24(2):185-187, 2006b.
Ludwig et al., *Nat. Methods*, 3(8):637-46, 2006a.
Manipulating the Mouse Embryo A Laboratory Manual, Second Edition, Cold Spring Harbor Laboratory Press, 1994.
Martin, *Proc. Natl. Acad. Sci. USA*, 78:7634, 1981.
Marvin et al., *Genes Dev.*, 15:316, 2001.
Miyoshi et al, *J. Biomater. Sci. Polym. Ed.*, 9:227-237, 1998.
Nakajima et al., *Cancer Chemother. Pharmacol.*, 52:319-324, 2003.
Nakano et al., *Science*, 272, 722, 1996.
Narazaki et al., *Circulation*, 118(5): 498-506, 2008.
Ockerman, *Clin. Chim. Acta*, 17:201, 1968.
Ogawa et al., *J. Cell Sci.*, 120:55-65, 2007.
Passonneau and Lauderdale, *Anal. Biochem.*, 60:405-415, 1974.
PCT Appln. WO 1998/30679
PCT Appln. WO 2001/088100
PCT Appln. WO 2001/51616
PCT Appln. WO 2002/076976
PCT Appln. WO 2003/004626
PCT Appln. WO 2003/050251
PCT Appln. WO 2003/059913
PCT Appln. WO 2003/062225
PCT Appln. WO 2003/062227
PCT Appln. WO 2004/039796
PCT Appln. WO 2005/080554
PCT Appln. WO 2005/123902
Properties and uses of Embryonic Stem Cells: Prospects for Application to Human Biology and Gene Therapy, 1998.
Rossi et al., *Cell*, 132:681-696, 2008.
Sasaki et al., *Pharmacol. Ther.*, 93:225-232, 2002.
Scalia et al., *J. Cell. Biochem.*, 82:610, 2001.
Schneider et al., *Genes Dev.*, 15:304, 2001.
Sheehan and Hrapchak, In: *Theory and Practise of Histotechnology*, 2nd Ed., Battelle Memorial Institute, Columbus, Ohio, 1987.
Shiojiri, *J. Embryol. Exp. Morph.*, 62:139, 1981.
Smith, In: *Origins and Properties of Mouse Embryonic Stem Cells*, Annu. Rev. Cell. Dev. Biol., 2000.
Suzuki et al., *Proc. Natl. Acad. Sci. USA*, 103:10294-10299., 2006.
Takahashi and Yamanaka, *Cell.*, 126(4):663-676, 2006.
Takahashi et al., *Cell*, 126(4):663-76, 2007.
Takahashi et al., *Cell*, 131:861-872, 2007.
Thompson, In: *Selected Histochemical and Histopathological Methods*, Tomas (Ed.), Sprungfield, Ill., 1966.
Thomson and Marshall, *Curr. Top. Dev. Biol.*, 38:133-165, 1998.
Thomson and Odorico, *Trends Biotechnol.*, 18(2):53-57, 2000.
Thomson et al. *Proc. Natl. Acad. Scie. USA*, 92:7844-7848, 1995.
Thomson et al., *Science*, 282:114, 1998.
van der Laarse et al., *Biotech Histochem.* 67:303, 1992.
Watabe and Miyazono, *Cell Res.*, 19:103-115, 2009.
Watanabe et al., *Nature Neurosci.*, 8:288-296, 2005.
Wobus et al., *Ann. N.Y. Acad. Sci.*, 27:752, 1995,
Xu et al., *Cell Stem Cell*, 3:196-206., 2008.
Xu et al., *Nat. Biotechnol.*, 19:971-974, 2001.
Yasmineh et al., *Clin. Biochem.*, 25:109, 1992.
Ying et al., *Cell*, 115:281-292, 2003.
Yu and Thompson, *Genes Dev.* 22(15):1987-97, 2008.
Yu et al., *Science*, 318:1917-1920, 2007.
Yu et al., *Science*, 324(5928):797-801, 2009.
Zhang, et al., *Zhongguo Xiu Fu Chong Jian Wai Ke Za Zhi.*, 23(1):82-86, 2009.

What is claimed is:

1. A method for differentiating human pluripotent stem cells from a human pluripotent stem cell clone into a chosen cell lineage, comprising the steps of:

a) obtaining a human pluripotent stem cell clone prepared from an individual human pluripotent stem cell, the human stem cell clone being either a human embryonic stem cell clone or a human induced pluripotent stem cell clone;

b) obtaining a batch of culture media;

c) culturing human pluripotent stem cells from the pluripotent stem cell clone in a maintenance culture media prepared in a first amount of said batch of culture media, wherein the maintenance culture media maintains the human pluripotent stem cells in an undifferentiated stated without the presence of a fibroblast feed cell layer;

d) culturing human pluripotent stem cells in a second amount of said batch of culture media in the presence of one or more differentiation factors capable of differentiating the human pluripotent stem cells into said chosen cell lineage, thereby determining amounts of one or more differentiation factors required to differentiate the human pluripotent stem cells into said chosen cell lineage;

e) obtaining a differentiation media comprising the amounts of one or more differentiation factors required to differentiate the human pluripotent stem cells into the chosen cell lineage, as determined in step d; and f) differentiating human pluripotent stem cells in the differentiation medium of step e, thereby differentiating human pluripotent stem cells from a human pluripotent stem cell clone into a chosen cell lineage.

2. The method of claim 1, wherein the human pluripotent stem cell clone is a human induced pluripotent stem cell clone.

3. The method of claim 1, wherein the chosen cell lineage is a neuron cell lineage.

4. The method of claim 1, wherein the chosen cell lineage is a hepatocyte cell lineage.

5. The method of claim 1, wherein step d comprises testing varied amounts of the one or more differentiation factors during a test period.

6. The method of claim 5, wherein the varied amounts of the one or more differentiation factors are added to said second amount of said batch culture media at about day 3 to day 7 into the test period.

7. The method of claim 5, wherein the varied amounts of the one or more differentiation factor comprises varying concentrations of BMP, Activin, BMP signaling inhibitor, and/or Activin signaling inhibitor that are capable of providing varied ratios of BMP/Activin signaling activity in the human pluripotent stem cells.

8. The method of claim 7, wherein the varied concentrations comprise varied concentrations of BMP4 alone, varied concentrations of Activin A alone, varied concentrations of BMP signaling inhibitor, varied concentrations of Activin signaling inhibitor, and varied concentrations of a combination of BMP4 and Activin A.

9. The method of claim 7, wherein step d further comprises measuring mesoderm or cardiac differentiation efficiency for varied ratios and choosing a ratio with the highest differentiation efficiency as representing the amounts of one or more differentiation factors required to differentiate the human pluripotent stem cells of step c into the chosen cell lineage, wherein the chosen cell lineage is cardiomyocytes.

10. The method of claim 9, wherein said measuring mesoderm differentiation efficiency comprises measuring mesoderm marker expression at about days 6, 7or 8 after differentiation.

11. The method of claim 10, wherein the mesoderm marker comprises KDR, PDGFR-a, CXCR4, CKIT$^{negtive}$, N-Cadherin, and/or MESP1.

12. The method of claim 9, wherein said measuring cardiac differentiation efficiency comprises measuring cardiomyocyte marker expression at about day 14 after differentiation.

13. The method of claim 1, wherein the differentiation medium has been prepared from the selected batch of culture medium by adjusting amounts or timing of addition of one or more differentiation factors.

14. The method of claim 13, further comprising determining amounts or timing of addition of one or more differentiation factors appropriate for differentiation into neurons.

15. The method of claim 14, wherein step d comprises testing amounts of the one or more differentiation factors capable differentiating the human pluripotent stem cells of step c along a neural cell lineage during varied test periods.

16. The method of claim 14, wherein said differentiation factors include BMP signaling inhibitor, and/or Activin signaling inhibitor.

17. The method of claim 15, wherein said varied test periods are varied periods prior to differentiation.

18. The method of claim 15, wherein varied test periods include two or more of the following conditions: day 5 prior to differentiation to day 0, day 4 prior to differentiation to day 0, day 3 prior to differentiation to day 0, day 2 prior to differentiation to day 0, and day 1prior to differentiation to day 0.

19. The method of claim 15, wherein said testing comprises measuring neural differentiation efficiency for each test period and selecting the test period with the highest differentiation efficiency as being appropriate for the differentiation of the human pluripotent stem cells into neurons.

20. The method of claim 19, comprising differentiating the stem cells into neurons in a differentiation medium, wherein the differentiation medium has been prepared by adding differentiation factors during the selected test period.

21. The method of claim 4, wherein step d comprises testing the one or more differentiation factors capable of differentiation the human pluripotent stem cells of c into hepatocytes.

22. The method of claim 21, wherein said testing comprises applying varied amounts of the one or more differentiation factors during a test period.

23. The method of claim 22, wherein the varied amounts of the one or more differentiation factors are added about day 1 to day 3 of the test period.

24. The method of claim 22, wherein the varied amounts of the one or more differentiation factor comprises varying concentrations of BMP, Activin, BMP signaling inhibitor, and/or Activin signaling inhibitor that are capable of providing varied ratios of BMP/Activin signaling activity in the human pluripotent stem cells.

25. The method of claim 24, wherein the varied concentrations comprise varied concentrations of BMP4 alone, varied concentrations of Activin A alone, varied concentrations of BMP signaling inhibitor, varied concentrations of Activin signaling inhibitor, and varied concentrations of a combination of BMP4 and Activin A.

26. The method of claim 24, wherein step d further comprises measuring endoderm or hepatocyte differentiation efficiency for the varied ratios and selecting a ratio with the highest differentiation efficiency as representing the amounts of one or more differentiation factors required to differentiate the human pluripotent stem cells of step c into hepatocytes.

27. The method of claim 26, wherein said measuring differentiation efficiency comprises measuring endoderm marker expression.

28. The method of claim 1, wherein differentiating the human pluripotent stem cells comprises forming aggregates of about 10 to 400 μm in diameter.

29. The method of claim 1, wherein the human pluripotent stem cells or progeny thereof are incubated in suspension culture.

30. The method of claim 29, wherein the suspension culture has a volume of from 5 milliliters to 25 liters.

31. The method of claim 29, wherein the suspension culture is rotated or shaken at a speed of 15 rpm to 100 rpm.

32. The method of claim 1, wherein the pluripotent stem cells or progeny cells thereof contain one or more transgenes.

33. The method of claim 32, wherein the one or more transgenes encode a selectable and/or screenable marker under the control of a promoter specific for the chosen cell lineage.

34. The method of claim 1, further comprising enriching or purifying the cells differentiated into the chosen cell lineage.

35. The method of claim 1, wherein the differentiation medium comprises bFGF at an amount of from 5 to 200 ng/ml.

36. The method of claim 1, wherein the batch of culture medium is a batch of culture medium selected from the group of culture media consisting of: TeSR, mTeSR, RPMI, supplemented DMEM-F12, or dilutions thereof.

37. The method claim 7, wherein said BMP signaling inhibitor comprises dorsomorphin and said Activin signaling inhibitor comprises SB431542.

* * * * *